(12) United States Patent
Xi et al.

(10) Patent No.: US 11,161,736 B2
(45) Date of Patent: Nov. 2, 2021

(54) VERSATILE, FLEXIBLE AND BIOCOMPATIBLE ELASTOMERIC MICROTUBES

(71) Applicants: National University of Singapore, Singapore (SG); Massachusetts Institute of Technology, Cambridge, MA (US); Shanghai Jiao Tong University, Shanghai (CN)

(72) Inventors: Wang Xi, Singapore (SG); Chwee Teck Lim, Singapore (SG); Fang Kong, Singapore (SG); Xiaobo Gong, Shanghai (CN)

(73) Assignees: National University of Singapore, Singapore (SG); Massachusetts Institute of Technology, Cambridge, MA (US); Shanghai Jiao Tong University, Shanghai (CN)

( * ) Notice: Subject to any disclaimer, the term of this patent is extended or adjusted under 35 U.S.C. 154(b) by 342 days.

(21) Appl. No.: 16/078,896

(22) PCT Filed: Mar. 2, 2017

(86) PCT No.: PCT/US2017/020443
§ 371 (c)(1),
(2) Date: Aug. 22, 2018

(87) PCT Pub. No.: WO2017/151915
PCT Pub. Date: Sep. 8, 2017

(65) Prior Publication Data
US 2019/0062152 A1    Feb. 28, 2019

Related U.S. Application Data

(60) Provisional application No. 62/302,919, filed on Mar. 3, 2016.

(51) Int. Cl.
*B29C 41/14* (2006.01)
*B81C 1/00* (2006.01)
(Continued)

(52) U.S. Cl.
CPC .......... *B81C 1/00134* (2013.01); *A61L 27/18* (2013.01); *A61L 27/50* (2013.01);
(Continued)

(58) Field of Classification Search
CPC . B29C 41/14; B29C 41/42; B29L 2031/7532; B81C 1/00134; C08L 15/00;
(Continued)

(56) References Cited

U.S. PATENT DOCUMENTS

2007/0013869 A1   1/2007   Dahi et al.
2015/0351967 A1  12/2015   Lim et al.
2020/0025699 A1   1/2020   Yeo et al.

FOREIGN PATENT DOCUMENTS

CN          1930513        3/2007
CN       103331754 A      10/2013
(Continued)

OTHER PUBLICATIONS

Extended Search Report for European Application No. 177608155, "Versatile, Flexible and Biocompatible Elastomeric Microtubes", dated Sep. 10, 2019.
(Continued)

*Primary Examiner* — Ryan M Ochylski
(74) *Attorney, Agent, or Firm* — Hamilton, Brook, Smith & Reynolds, P.C.

(57) ABSTRACT

The present invention relates to a flexible polymer-based microtube having an inner diameter of about 4 μm to about 1000 μm and a variable outer diameter, wherein the cross-sectional shape of the microtube can be, for instance, circular, rectangular, square, triangular, elliptical, star or
(Continued)

irregular. The present invention also relates to a method of making the flexible microtube and devices incorporating the flexible microtube.

12 Claims, 12 Drawing Sheets

(51) Int. Cl.

| | | |
|---|---|---|
| A61L 27/60 | (2006.01) | |
| A61L 27/18 | (2006.01) | |
| A61L 27/50 | (2006.01) | |
| B29C 41/42 | (2006.01) | |
| C08L 15/00 | (2006.01) | |
| C08L 75/04 | (2006.01) | |
| C08L 79/08 | (2006.01) | |
| C08L 83/04 | (2006.01) | |
| C12M 3/06 | (2006.01) | |
| A61F 2/10 | (2006.01) | |
| B29L 31/00 | (2006.01) | |

(52) U.S. Cl.
CPC .............. *A61L 27/507* (2013.01); *A61L 27/60* (2013.01); *B29C 41/14* (2013.01); *B29C 41/42* (2013.01); *C08L 15/00* (2013.01); *C08L 75/04* (2013.01); *C08L 79/08* (2013.01); *C08L 83/04* (2013.01); *A61F 2/105* (2013.01); *B29K 2995/0026* (2013.01); *B29K 2995/0056* (2013.01); *B29K 2995/0065* (2013.01); *B29L 2031/7532* (2013.01); *B81C 2201/038* (2013.01); *C08L 2203/02* (2013.01); *C12M 23/16* (2013.01)

(58) Field of Classification Search
CPC .......... C08L 75/04; C08L 79/08; C08L 83/04; C08L 2203/02
See application file for complete search history.

(56) References Cited

FOREIGN PATENT DOCUMENTS

| | | |
|---|---|---|
| CN | 104340956 | 2/2015 |
| CN | 104445055 | 3/2015 |
| CN | 104936566 | 9/2015 |
| CN | 105444928 A | 3/2016 |
| CN | 106197773 A | 12/2016 |
| EP | 1557396 A2 | 7/2005 |
| JP | S62192171 A | 8/1987 |
| JP | 5304021 H | 11/1993 |
| JP | H07328127 A | 12/1995 |
| JP | 2008248181 A | 10/2008 |
| JP | 2009537439 | 10/2009 |
| WO | 2011028579 | 3/2011 |
| WO | 2013044226 A2 | 3/2013 |
| WO | 2016019087 | 2/2016 |
| WO | WO 2018/160135 | 9/2018 |

OTHER PUBLICATIONS

Paek, J., et al., "Microrobotic tentacles with spiral bending capability base4d on shape-engineered elastomeric microtubes", Scientific Reports, Jun. 11, 2015, 11 pages.
Gorissen, B., et al., "Modeling and bonding-free fabrication of fexible fluidic microactuators with a bending motion", J. Micromech. Microeng. 23 (2013) 045012 (10 pages).
Heng, X., et al., "Flexible PDMS microtubes for examining local hydrophobicity", Microsyst Technol (2015) 21: 477-485.
Paek, J., et al., "Spiraling Soft-Robotic Micro-Tentacles Based on Shape-Engineered, Highly Deformable Elastomeric Microtubes", 19th International Conference on Miniaturized Systems for Chemistry and Life Sciences, Oct. 25-29, 2015, Gyeongju, Korea, 3 pages.
Aboutalebi, S.H., et al., "High-Performance Multifunctional Graphene Yarns: Toward Wearable All-Carbon Energy Storage Textiles", ACS Nano, 2014, 11 pgs.
Atwa, Y., et al., "Silver nanowire coated threads for electrically conductive textiles", J. Mater. Chem. C., 2015, 3, 3908-3912.
Avolio, A. P., et al., "Role of Pulse Pressure Amplification in Arterial Hypertension", Hypertension 2009, 54, 375.
Bao, Z., et al., "Flexible and Stretchable Devices", Adv. Mater, 2016, 28, 4177-4179.
Cai, F., et al., "Ultrasensitive, passive and wearable sensors for monitoring human muscle motion and physiological signals", Biosensors and Bioelectronics 77 (2016) 907-913.
Cai, G., et al., "Extremely Stretchable Strain Sensors Based on Conductive Self-Healing Dynamic Cross-Links Hydrogels for Human-Motion Detection", Adv. Sci. 2017, 4, 1600190.
Chen, L. Y., et al., "Continuous Wireless Pressure Monitoring and Mapping with Ultra-Small Passive Sensors for Health Monitoring and Critical Care", Nat. Commun. 2014, 5.
Choong, C-L., et al., "Highly Stretchable Resistive Pressure Sensors Using a Conductive Elastomeric Composite on a Micropyramid Array", Adv. Mater. 2014, 26, 3451-3458.
Chortos, Al., et al., "Pursuing prosthetic electronic skin", Nature Materials vol. 15, Sep. 2016, 937-950.
Deguchi, S., et al., "Viscoelastic and optical properties of four different PDMS polymers", Journal of Micromechanics and Microengineering 2015, 25, 097002, 7 pages.
Do, T. N. et al., Stretchable, Twisted Conductive Microtubules for Wearable Computing , Robotics, Electronics, and Healthcare. Scientific Reports, May 11, 2017, vol. 7, No. 1753, pp. 1-12.
Gao, W., et al., "Fully integrated Wearable sensor arrays for multiplexed in situ perspiration analysis", Nature, Jan. 28, 2016; 529(7587): 509-514.
Gong, S., et al., "Tattoolike Polyaniline Microparticle-Doped Gold Nanowire Patches as Highly Durable Wearable Sensors", ACS Appl. Mater. Interfaces, Aug. 2015, 9 pages.
Gong, S., et al., "A wearable and highly sensitive pressure sensor with ultrathin gold nanowires", Nature Communications 2014, 5, 3132.
Hammock, M.L., et al., "25th Anniversary Article: The Evolution of Electronic Skin (E-Skin): A Brief History, Design Considerations and Recent Progress" Adv. Mater. 2013, 25, 5997-6038.
Han, S., et al., "Mechanically Reinforced Skin-Electronics with Networked Nanocomposite Elastomer", Adv. Mater. 2016, 28, 10257-10265.
Harada, S., et al., "Fully Printed Flexible Fingerprint-like Three-Axis Tactile and Slip Force and Temperature Sensors for Artificial Skin", ACS Nano 2014, 8 (12), 12851-12857.
Huang, S., et al., "Electroeposition of polypyrrole on carbon nanotube-coated cotton fabrics for all-solid flexible supercapacitor electrodes", Royal Society of Chemistry, 2013, 8 pages.
Hyun, W.J., et al, "High-Resolution Patterning of Graphene by Screen Printing with a Silicon Stencil for Highly Flexible Printed Electronics", Adv. Mater. 2015, 27, 109-115.
International Preliminary Report on Patentability for International Application No. PCT/SG2018/050076, "Microtube Sensor for Physiological Monitoring", dated Sep. 3, 2019.
International Search Report for International Application No. PCT/SG2018/050076, "Microtube Sensor for Physiological Monitoring", dated May 14, 2018.
Jang, K-I., et al., "Rugged and breathable forms of stretchable electronics with adherent composite substrates for transcutaneous monitoring", Nat. Commun., 5:4779 doi: 10.1038/ncommos5779 (2014).
Jinno, H., et al., "Stretchable and waterproof elastomer-coated organic photovoltaics for washable electronic textile applications", Nature Energy, (Sep. 2017), 6 pages.
Johnston, I. D., et al., "Mechanical characterization of bulk Sylgard 184 for microfluidics and microengineering", Journal of Micromechanics and Microengineering 2014, 24, 035017.
Kang, S-K., et al., "Bioresorbable silicon electronic sensors for the brain", Nature, (2016) 1-9.

(56) References Cited

OTHER PUBLICATIONS

Kenry, et al., "Emerging flexible and wearable physical sensing platforms for healthcare and biomedical applications", Microsystems & Nanoengineering (2016) 2, 16043; doi:10.1038/micronano.2016.43.
Khondoker, M.A.H., et al., "Fabrication methods and applications of microstructured gallium based liquid metal alloys", Smart Mater. Struct. 25 (2016) 093001, 23 pages.
Kim, J., et al., "Stretchable silicon nanoribbon electronics for skin prosthesis", Nat. Commun., 5:5747 doi: 10.1038/ncomms6747 (2014).
Kim., D-H., "Epidermal Electronics", Science, 333, 838 (2011).
Kim., S., et al., "Stretching and Twisting Sensing with Liquid-Metal Strain Gauges Printed on Silicone Elastomers", IEEE Sensors Journal, Nov. 2015, 15(11): 6077-6078.
Le Floch, P., et al., "Wearable and Washable conductors for active textiles", ACS Applied Materials & Interfaces *Jul. 2011). DOI:10.1021/acsami.7b07361.
Lee, D., et al., "Highly Sensitive, Transparent, and Durable Pressure Sensors Based on Sea-Urchin Shaped Metal Nanoparticles", Ad. Mater. 2016, 28, 9364-9369.
Lee, H. K.; et al., "Normal and Shear Force Measurement Using a Flexible Polymer Tactile Sensor With Embedded Multiple Capacitors", Journal of Microelectromechanical Systems 2008, 17 (4), 934-942.
Lee, H., et al., "A graphene-based electrochemical device with thermoresponsive microneedles for diabetes monitoring and therapy", Nat Nano 2016, 11, 566-574.
Lee, J., et al., "Conductive Fiber-Based Ultrasensitive Textile Pressure Sensor for Wearable Electronics", Adv. Mater., 2015, 27, 2433-2439.
Lee, H, et al., "Soft Bioelectronics using Nanomaterials", Proc. SPIE 9945, Sep. 27, 2016, 12 pages.
Liang, S., et al., "3D Stretchable, Compressible, and Highly Conductive Metal-Coated Polydimethylsiloxane Sponges", Adv. Mater. Technol., 2016, 1, 1600117.
Li, R., et al., "Microflotronics: A Flexible, Transparent, Pressure-Sensitive Microfluidic Film", Advanced Functional Materials 2014, 24, 6195-6203.
Li, S., et al., "A Stretchable Multicolor Display and Touch Interface Using Photopatterning and Transfer Printing", Adv. Mater. 2016, 28, 9770-9775.
Li, Y., et al., "Cellulose-Nanofiber-Enabled 3D Printing of a Carbon-Nanotube Microfiber Network", Small Methods (2017), 1 (10), 1700222 (8 pages).
Li, Y., et al., "Highly Conductive Microfiber of Graphene Oxide Templated Carbonization of Nanofibrillated Cellulose", Adv. Funct. Mater. 2014, 24 (46), 7366-7372.
Liu, T., et al., "A Small and Low-Cost 3-D Tactile Sensor for a Wearable Force Plate", IEEE Sensors Journal 2009, 9 (9), 1103-1110.
Marin, S., et al., "Nanomaterials Based Electrochemical Sensing Applications for Safety and Security", Electroanalysis 2012, 24(3): 459-469.
Matsuhisa, N., et al., "Printable elastic conductors by in situ formation of silver nanoparticles from silver flakes", Nature Materials, (May 2017), 8 pages.
Matsuhisa, N., et al., "Printable elastic conductors with a high conductivity for electronic textile applications", Nature Communications, 6:7461, DOI: 10.1038/ncommas8461 (2015).
Nichols, W.W., "Clinical Measurement of Arterial Stiffness Obtained from Noninvasive Pressure Waveforms", American Journal of Hypertension 2005, 18, 3S.
Ota, H., et al., "Highly deformable liquid-state heterojunction sensors", Nature Communications, 2014, 5:5032.
Pan, Shaowu, et al., "Novel Wearable Energy Devices Based on Aligned Carbon Nanotube Fiber Textiles" Adv. Energy Mater., 2014, 1401438.
Park, D. Y., et al., "Self-Powered Real-Time Arterial Pulse Monitoring Using Ultrathin Epidermal Piezoelectric Sensors", Adv. Mater. 2017, 29 (37).
Park, M., et al., "MoS2-Based Tactile Sensor for Electronic Skin Applications", Adv. Mater. 2016, 28, 2556-2562.
Park, S., et al., "Soft, stretchable, fully implantable miniaturized optoelectronic systems for wireless optogenetics", Nat. Biotechnol. Dec. 2015; 33(12): 1280-1286. doi:10.1038/nbt.3415.
Park, Y.-L., et al., "Hyperelastic pressure sensing with a liquid-embedded elastomer", Journal of Micromechanics and Microengineering 2010, 20 (12), 125029.
Piwek, L., et al., "The Rise of Consumer Health Wearables: Promises and Barriers", PLOS Med 13(2): e1001953. doi:10.1371/journal.pmed.1001953. (Feb. 2, 2016).
Quéré, D., "Fluid Coating on a Fiber", Annual Review of Fluid Mechanics 1999, 31, 347-384.
Ramachandran, T.; Vigneswaran, C. Design and Development of Copper Core Conductive Fabrics for Smart Textiles. J. Ind. Text. 2009, 39 (1), 81-93.
Ryan, J.D., "Machine-Washable PEDOT:PSS Dyed Silk Yarns for Electronic Textiles", ACS Appl. Mater. Interfaces 2017, 9, 9045-9050.
Schwartz, G., et al., "Flexible polymer transistors with high pressure sensitivity for application in electronic skin and health monitoring", Nat. Commun., 4:1859 doi:10.1038/ncomms2832 (2013).
Sharma, B., et al., "Load-Controlled Roll Transfer of Oxide Transistors for Stretchable Electronics", Adv. Mater. 2013, 23, 2024-2032.
Shyamkumar, P., et al., "Wearable Wireless Cardiovascular Monitoring Using Textile-Based Nanosensor and Nanomaterial Systems", Electronics, 2014, 3, 504-520.
Silverman, I. K., et al., "Displacements in closed circular rings subject to concentrated diametral loads", Journal of the Franklin Institute, 279(5), May 1965, 374-386.
Song, S-H., et al., "A rapid and simple fabrication method for 3-dimensional circular microfluidic channel using metal wire removal process", Microfluid Nanofluid (2010) 9: 533-540.
Stoppa, M., et al., "Wearable Electronics and Smart Textiles: A Critical Review", Sensors, 2014, 14, 11957-11992.
Tao, X., et al., "How to Make Reliable, Washable, and Wearable Textronic Devices", Sensors, 2017, 17, 673, 16 pages.
Wang, K., et al., "High-Performance Two-Ply Yarn Supercapacitors Based on Carbon Nanotubes and Polyaniline Nanowire Arrays", Ad. Mater. 2013, 25, 1494-1498.
Wang, X., et al., "Self-Powered High-Resolution and Pressure-Sensitive Triboelectric Sensor Matrix for Real-Time Tactile Mapping", Adv. Mater. 2016.
Written Opinion for International Application No. PCT/SG2018/050076, "Microtube Sensor for Physiological Monitoring", dated May 14, 2018.
Xi, W., et al., "Soft Tubular Microfluidics for 2D and 3D Applications", Proc. Natl. Acad. Sci. 2017, 114 (40), 10590-10595.
Yan H., et al., "Coaxial printing method for directly writing stretchable cable as strain sensor", Appl. Phys. Lett., Aug. 23, 2016, vol. 109, pp. 083502-1-083502-4.
Yang, H., et al., "Soft Thermal Sensor with Mechanical Adaptability", Adv. Mater. 2016, 28, 9175-9181.
Yang, T. et al., "A Wearable and Highly Sensitive Graphene Strain Sensor for Precise Home-Based Pulse Wave Monitoring", ACS Sensors 2017, 2 (7), 967-974.
Yap, L.W., et al., "Soft piezoresistive pressure sensing matrix from copper nanowires composite aerogel", Sci. Bull. (2016) 61(20): 1624-1630.
Yeo, J.C., et al., "Flexible and Stretchable Strain Sensing Actuator for Wearable Soft Robotic Applications", Adv. Mater. Technol. 2016, 1600018, 9 pages.
Yeo, J.C., et al., "Triple-State Liquid-Based Microfluidic Tactile Sensor with High Flexibility, Durability, and Sensitivity", ACS Sens., Mar. 2016, 9 pages.
Yeo, J.C., et al., "Wearable tactile sensor based on flexible microfluidics", Lab Chip, 2016, 16, 3244-3250.
Yildiz, S.K., et al., "Fabricaion and characterisation of highly stretchable elastomeric strain sensors for prosthetic hand applications", Sensors and Actuators A: Physical, 247, 514-521 (2016).

(56) References Cited

OTHER PUBLICATIONS

Yu, P.Y., et al., "Flexible Piezoelectric Tactile Sensor Array for Dynamic Three-Axis Force Measurement" Sensors 2016, 16, 819, 15 pages.
Yue Fei, J., et al., "PDMS microchannel fabrication technique based on microwire-molding", Chinese Science Bulletin, Dec. 2008, 53(4): 3928-3936.
Yun, Y. J. et al., "Highly Conductive and Environmentally Stable Gold/graphene Yarns for Flexible and Wearable Electronics", Nanoscale 2017, 9 (32), 11439-11445.
Yun, Y.J., et al., "A Novel Method for Applying Reducted Graphene Oxide Directly to Electronic Textiles from Yarns to Fabrics", Adv. Mater. 2013, 25, 5701-5705.
Zhang, H., et al., "Piezoresistive Sensor with High Elasticity Based on 3D Hybrid Network of Sponge@CNTs@Ag NPs", ACS Appl. Mater. Interfaces 2016, 8, 22374-33281.
Zhu, S. et al., "Ultrastretchable Fibers with Metallic Conductivity Using a Liquid Metal Alloy Core", Advanced Functional Materials 2013, 23 (18), 2308-2314.
Chinese Search Report for Chinese Application No. 201780020857.1, "Versatile, Flexible and Biocompatible Elastomeric Microtubes", dated Jun. 17, 2020.
Colas, A., "Silicone Biomaterials: History and Chemistry", Chimie Nouvelle 1990, 8 (30), 847.
Abdelgawad, M., et al., "A fast and simple method to fabricate circular microchannels in polydimethylsiloxane (PDMS)", Lab Chip 2011, 11 (3), 545-551.
Lee, J., et al., "Sucrose-based fabrication of 3D-networked, cylindrical microfluidic channels for rapid prototyping of lab-on-a-chip and vaso-mimetic devices", Lab Chip 2012, 12 (15), 2638-2642.
De Ville, M., et al., "Simple and low-cost fabrication of PDMS microfluidic round channels by surface-wetting parameters optimization", Microfluid Nanofluid, 2012, 12 (6), 953-961.
Kolesky, D. B., et al., "3D Bioprinting of Vascularized, Heterogeneous Cell-Laden Tissue Constructs", Adv. Mater. 2014, 26 (19), 3124-3130.
Bhargava, et al., N., "Discrete elements for 3D microfluidics", Proc. Natl. Acad. Sci. USA 2014, 111 (42), 15013-15018.
Au, A. K., et al., "Mail-order microlluidics: evaluation of stereolithography for the production of microfluidic devices", Lab Chip 2014, 14 (7), 1294-1301.
Miller, J. S., et al., "Rapid casting of patterned vascular networks for perfusable engineered three-dimensional tissues", Nat. Mater 2012, 11 (9), 768-774.
Kitson, P. J., et al., "Configurable 3D-Printed millifluidic and microfluidic 'lab on a chip' reactionware devices", Lab Chip 2012, 12 (18), 3267-3271.
Derby, B., "Printing and Prototyping of Tissues and Scaffolds", Science 2012, 338 (6109), 921-926.
Schmidt, O. G.; Eberl, K., "Nanotechnology: Thin solid films roll up into nanotubes", Nature 2001, 410 (6825), 168-168.
Xi, W., et al., "Rolled-up Functionalized Nanomembranes as Three-Dimensional Cavities for Single Cell Studies", Nano Lett. 2014, 14 (8), 4197-4204.
Harazim, S. M., et al., "Lab-in-a-tube: on-chip integration of glass optofluidic ring resonators for label-free sensing applications", Lab Chip 2012, 12 (15), 2649-2655.
Unger, M. A., et al., "Monolithic Microfabricated Valves and Pumps by Multilayer Soft Lithography", Science 2000, 288 (5463), 113-116.

Bhatia, S. N., et al., "Microfluidic organs-on-chips", Nat. Biotech. 2014, 32 (8), 760-772.
Zervantonakis, I. K., et al., "Three-dimensional microfluidic model for tumor cell intravasation and endothelial barrier function", Proc. Natl. Acad. Sci. USA 2012, 109 (34), 13515-13520.
Englert, D. L., et al., "Investigation of bacterial chemotaxis in flow-based microfluidic devices", Nat. Protocols 2010, 5 (5), 864-872.
Weaver, J. A., et al., "Static control logic for microfluidic devices using pressure-gain valves", Nat Phys 2010, 6 (3), 218-223.
Wong, A. D. et al., "Live-Cell Imaging of Invasion and Intravasation in an Artificial Microvessel Platform", Cancer Res. 2014, 74 (17), 4937-4945.
Whitesides, G. M., "The origins and the future of microfluidics", Nature 2006, 442 (7101), 368-373.
Grilli, S., et al., "3D lithography by rapid curing of the liquid instabilities at nanoscale", Proc. Natl. Acad. Sci. USA 2011, 108 (37), 15106-15111.
Lee, J., et al., "Elastomeric microwire-based optical gas flowmeter with stretching-enabled tunability in measurement range", Opt. Lett. 2011, 36 (19), 3789-3791.
Au, A. K, et al., "3D-printed microfluidic automation", Lab Chip 2015, 15 (8), 1934-1941.
Rogers, C. I., et al., "3D printed microfluidic devices with integrated valves", Biomicrolluidics 2015, 9 (1), 016501.
Goldsmith, H. L., et al., "Margination of leukocytes in blood flow through small tubes", Microvasc. Res. 1984, 27 (2), 204-222.
Cantat, I., et al., "Lift Force and Dynamical Unbinding of Adhering Vesicles under Shear Flow", Phys. Rev. Lett. 1999, 83 (4), 880-883.
Kumar, A., et al., "Mechanism of Margination in Confined Flows of Blood and Other Multicomponent Suspensions", Phys. Rev. Lett. 2012, 109 (10), 108102.
Hou, H. W., et al., "Isolation and retrieval of circulating tumor cells using centrifugal forces", Sci. Rep. 2013, 3, 1-8.
Warkiani, M. E., et al., "Slanted spiral microfluidics for the ultrafast, label-free isolation of circulating tumor cells", Lab Chip 2014, 14 (1), 128-137.
Kalpakli, A., et al., "Dean vortices in turbulent flows: rocking or rolling?", J Vis 2012, 15 (1), 37-38.
Kalpakli, A. "Experimental study of turbulent flows through pipe bends", PhD Thesis, KTH Mechanics, Stockholm, Sweden, 2012.
Di Carlo, D., et al., "Continuous inertial focusing, ordering, and separation of particles in microchannels", Proc. Natl. Acad. Sci. USA 2007, 104 (48), 18892-18897.
Davis, J. A., et al., "Deterministic hydrodynamics: Taking blood apart", Proc. Natl. Acad. Sci. USA 2006, 103 (40), 14779-14784.
Teh, S.-Y., et al., "Droplet microfluidics", Lab Chip 2008, 8 (2), 198-220.
Atencia, J., et al., "Controlled microfluidic interfaces", Nature 2005, 437 (7059), 648-655.
Notification of Transmittal of the International Search Report and the Written Opinion of the International Searching Authority, or the Declaration for International Application No. PCT/US2017/20443, "Versatile, Flexible and Biocompatible Elastomeric Microtubes", dated May 16, 2017.
Notification Concerning Transmittal of International Preliminary Report on Patentability for International Application No. PCT/US2017/020443, "Versatile, Flexible and Biocompatible Elastomeric Microtubes", dated Sep. 13, 2018.
Supplementary European Search Report for EP Application No. EP 18 76 0838, "Microtube Sensor for Physiological Monitoring" dated Nov. 5, 2020.

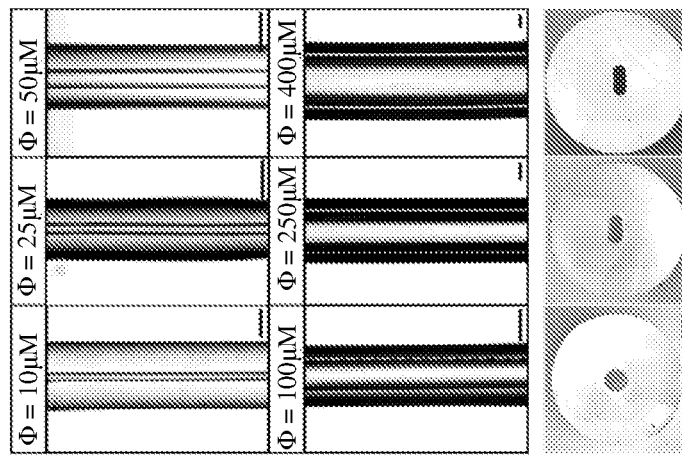
FIG. 1B
FIG. 1C
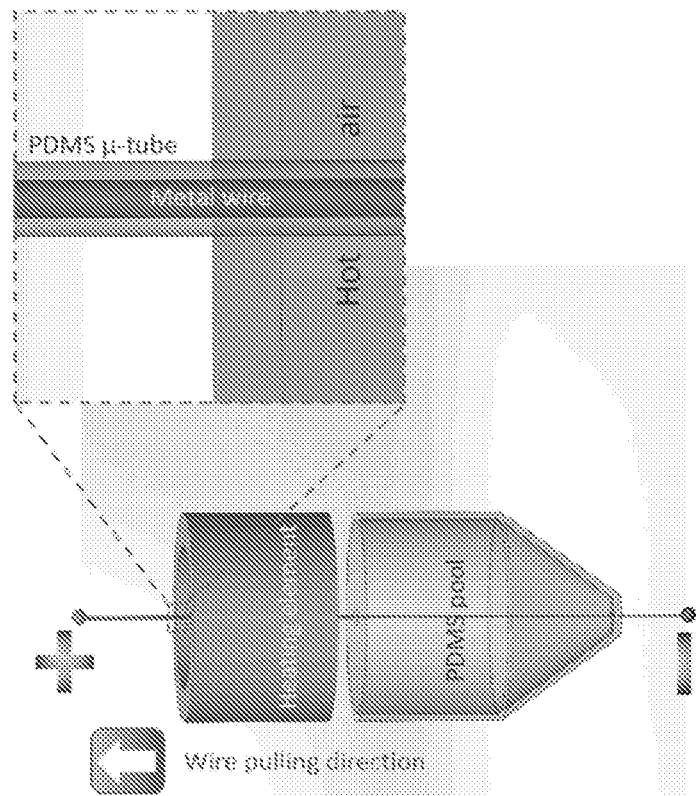
FIG. 1A

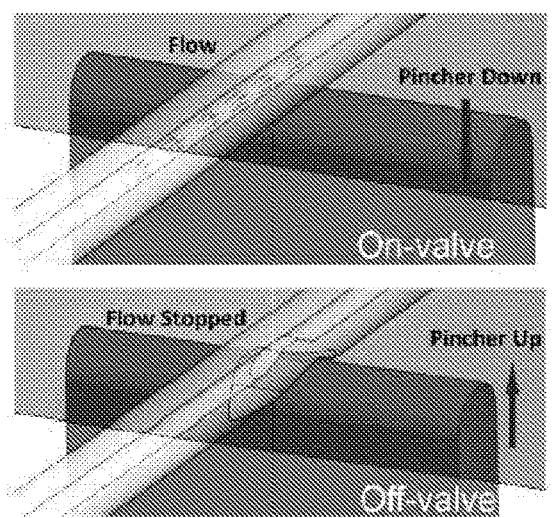 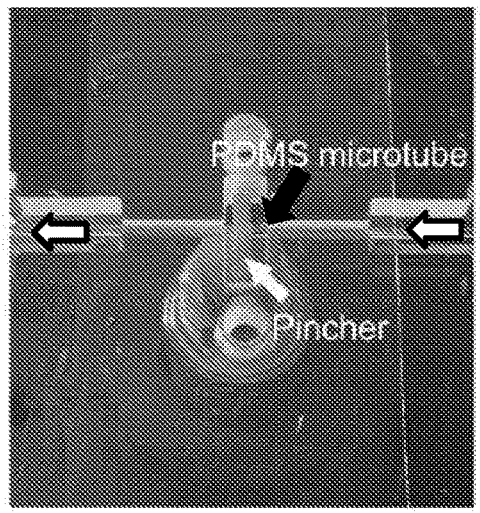
FIG. 6A  FIG. 6B
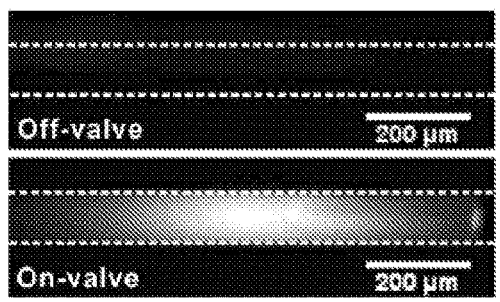
FIG. 6C
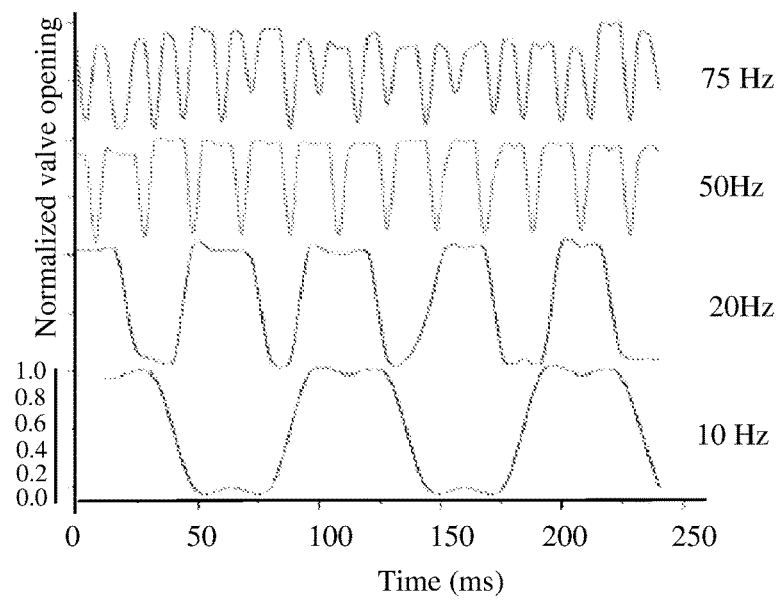
FIG. 6D

VERSATILE, FLEXIBLE AND BIOCOMPATIBLE ELASTOMERIC MICROTUBES

RELATED APPLICATION

This application claims the benefit of U.S. Provisional Application No. 62/302,919 filed on Mar. 3, 2016. The entire teachings of the above application are incorporated herein by reference.

BACKGROUND

Microfluidics devices made of elastomeric materials such as polydimethylsiloxane (PDMS) normally consist of microfluidic channels specifically designed to perform tasks such as microscale manipulation, analysis and sorting of micro and nanoscale entities such as biomolecules, cells and particles. However, the conventional fabrication of microfluidics always involves the complicated photolithography process which is expensive, limits microfluidic channel geometry to rectangular cross-section and is difficult to form complex three-dimensional (3D) microstructures. All these pose a barrier for the wider adoption of this technique.

SUMMARY OF THE INVENTION

Novel, inexpensive and efficient methods to fabricate microfluidic tubes (microtubes) from a variety of elastomeric materials are described. These microtubes have an inner diameter that can range from about 4 μm to about 1000 μm and an outer diameter that is variable and can be controlled depending on needs. The length of the microtubes can be varied depending on the end use. The microtubes can have any desired cross-sectional shape, for example, circular, rectangular, square, triangular, elliptical, star or irregular. Using these elastomeric microtubes as basic building blocks, it is now possible to design and produce microfluidic devices without the need for photolithography. This not only radically changes the way one designs and builds microfluidic devices, but also provides the versatility to alter the design of the microfluidic devices at will without the need to redesign and refabricate the whole microfluidic device again. Instead, these microtubes can be added or removed to make changes to the design of the microfluidic device which can be in two-dimensional (2D) or even 3D in configuration. The ability of these elastic microtubes to be assembled and disassembled enables the fast patterning of microchannels into almost any architecture as needed and when desired. Consequently, significant reductions in costs have been seen, as well as a significant reduction in the time taken to design, build and test these microfluidic devices. In addition, the microtubes can be biocompatible, flexible, gas permeable and highly transparent and make for an excellent candidate for producing biomedical devices for various applications, e.g., flexible microfluidics, artificial skins, organs-on-chips, blood vessel and capillary network mimicking, opto-microfluidics and 3D bioreactors, among others.

In a first aspect, the invention is a flexible microtube comprising a polymer, the microtube having an inner diameter of about 4 μm to about 1000 μm and a variable outer diameter. The cross-sectional shape of the microtube can be, for instance, circular, rectangular, square, triangular, elliptical, star or irregular.

In an embodiment of the first aspect, the polymer is a silicone elastomer, an ultraviolet sensitive polymer, a conductive polymer, a thermoplastic polymer, a thermoset polymer, a polyimide, a conductive rubber, or a polyurethane. The silicone elastomer can be, for instance, polydimethylsiloxane, phenyl-vinyl silicone, methyl-siloxane, fluoro-siloxane or platinum cured silicone rubber. The ultraviolet sensitive polymer can be, for instance, MYpolymer® (a fluorinated resin with acrylate/methacrylate groups produced by MY Polymers Ltd.), styrene-acrylate-containing polymer, polyacrylate polyalkoxy silane, a positive photoresist (e.g., diazonaphthoquinone-based positive photoresist) or a negative photoresist (e.g., epoxy-based negative photoresist).

In another embodiment of the first aspect, the microtube inner diameter is between about 10 μm and about 800 μm.

In another embodiment of the first aspect, the length of the microtube is about 10 m or less.

In another embodiment of the first aspect, the microtube is gas permeable.

In another embodiment of the first aspect, the microtube is transparent.

In another embodiment of the first aspect, the microtube is biocompatible.

In a second aspect, the invention is a method of making a flexible microtube comprising a polymer, the method comprising immersing a wire into a pool comprising heat curable polymer; heating the wire for a first period of time, thereby initiating curing of the heat curable polymer at the surface of the wire; pulling the wire out of the pool; heating the wire for a second period of time, thereby curing additional heat curable polymer and producing a polymer coated wire; immersing the polymer coated wire in a liquid bath with sonication, thereby loosening the polymer-wire contact; removing the wire from the polymer coated wire, thereby producing a polymeric microtube; and heating the polymeric microtube, thereby producing the flexible microtube of the first aspect.

In an embodiment of the second aspect, the heating for a first period of time is performed via electric current along the wire, the heating for a second period of time is performed via a hot air heating element, the liquid bath is an acetone bath, and the heating of the polymeric microtube is performed via baking.

In another embodiment of the second aspect, the method of making a flexible microtube comprises immersing a wire into a pool comprising a pre-cured ultraviolet-curable polymer, pulling the wire out of the pool and into an argon chamber, curing a layer of ultraviolet-curable polymer coated around the wire under an ultraviolet mercury lamp, thereby producing a polymer coated wire, immersing the polymer coated wire in a liquid bath with sonication, thereby loosening the polymer-wire contact, removing the wire from the polymer coated wire, thereby producing a polymeric microtube, and heating the polymeric microtube, thereby producing the flexible microtube of the first aspect.

In a third aspect, the invention is a device comprising the microtube of the first aspect.

In an embodiment of the third aspect, the device is a biomedical device.

In another embodiment of the third aspect, the biomedical device is an artificial skin, organ-on-chip, blood vessel mimicking device, capillary network mimicking device, opto-microfluidic device, a 3D bioreactor, drug delivery device, cell stretcher, tissue engineering scaffold, micropump or micro-valve.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

FIG. 1A is a schematic view of the experimental set-up for PDMS microtube fabrication.

FIG. 1B shows images of PDMS microtubes with circular cross-sections at different inner diameters (side-views, IDs are indicated by text at the top of each view, scale bars: 30 µm for ID ($\Phi$)=10 µm, 75 µm for $\Phi$=25 µm and 100 µm for the rest).

FIG. 1C shows transverse planes of tubes with varying cross-sectional shapes (scale bar: 250 µm).

FIG. 6A is a schematic presentation of an on-off valve using a PDMS microtube with ID=100 µm.

FIG. 6B is a photo of an on-off valve using a PDMS microtube with ID=100 µm wherein the valve is realized by periodically pressing a PDMS microtube (indicated by the black arrow) with a pincher (0.5 mm wide, indicated by the white-only arrow in (FIG. 6B)) to interfere the flow (indicated by the black-outlined-white arrows) inside.

FIG. 6C shows fluorescent images representing the off-valve and on-valve, respectively, as realized in FIG. 6B.

FIG. 6D is a graph of time response of opening and closing of the valve (100 µm inner diameter) at different frequencies wherein the opening and closing of the valve are indicated by the intensity of the fluorescence inside the tube (FIG. 6C) and the normalized fluorescent intensity varying as a function of time is shown, and wherein the abrupt increase and decrease in the fluorescent signal indicate fast response of the microtube to the mechanical compression with minimum delay and the valve functions reasonably well up to 75 Hz (the limit of the hardware).

DETAILED DESCRIPTION OF THE INVENTION

Figure 2A:
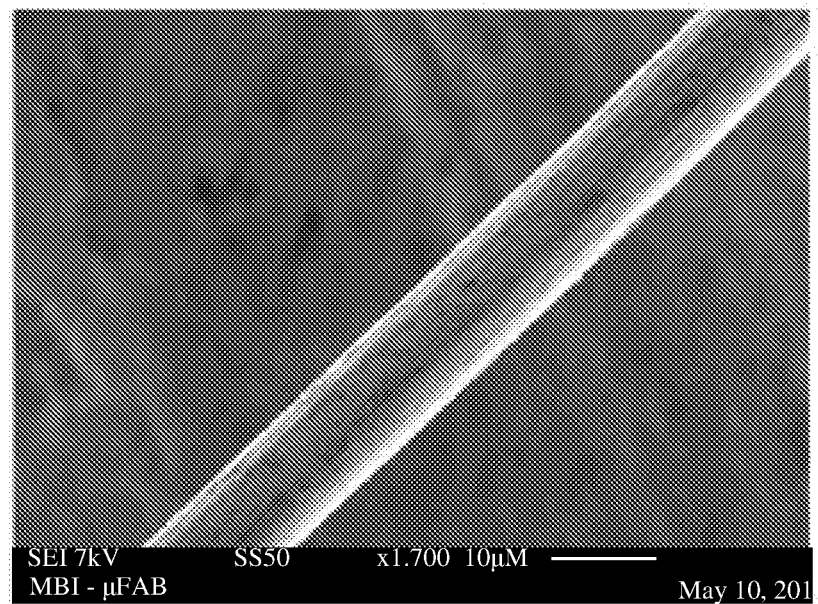
FIG. 2A shows an SEM image showing a tungsten wire with a diameter of 10 µm.
Figure 2B:
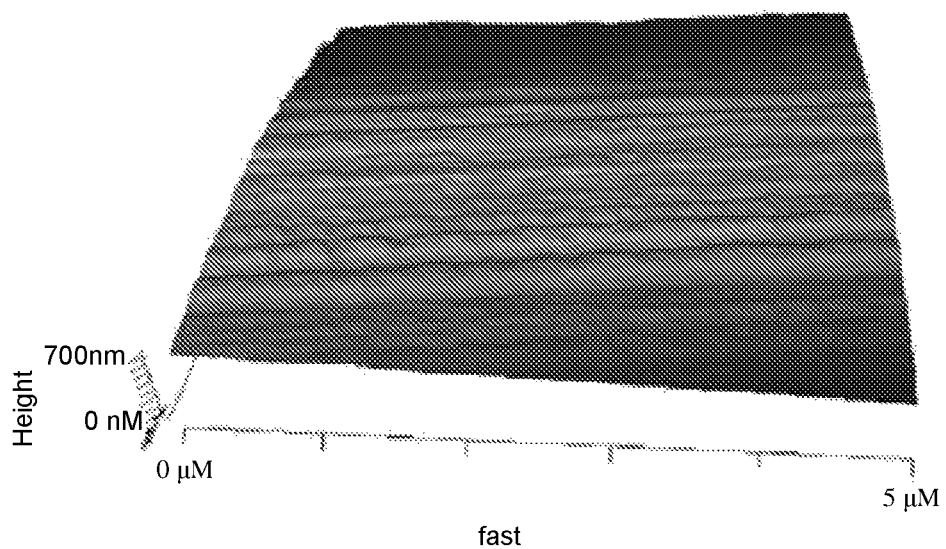
FIG. 2B shows an AFM topography presenting the surface of the tungsten wire.
Figure 2C:
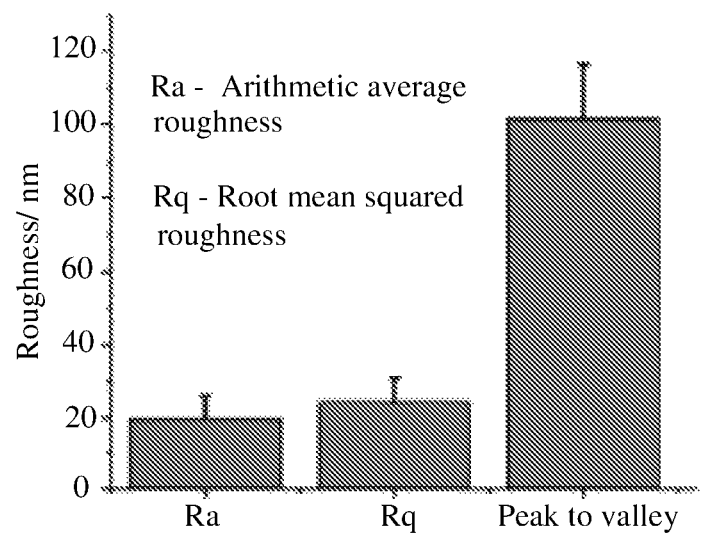
FIG. 2C shows the smoothness of the microtubes' inner surface and inner diameter.
Figure 2D:
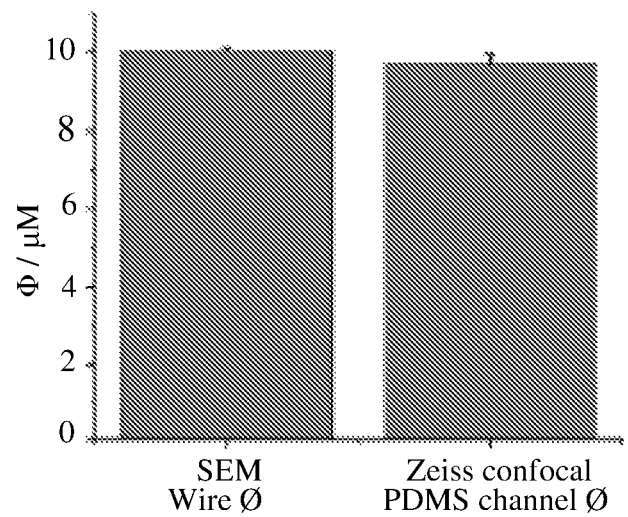
FIG. 2D shows a comparison between the wire diameter and the inner diameter of the PDMS microtube manufactured from the wire.

Commercially available silicone tubing is normally made by extrusion of compounded elastomers mixture, which is easily converted into 3D elastomers using a cross-linking reaction (cure). Two reactions are preferred:[1] 1) peroxide initiated and 2) platinum catalysed. In both cases, the precursors are mixed at the point of use before extrusion at room temperature followed by continuous curing in high temperature ovens. Different dies and mandrels are used to produce single-lumen tubing of various size and wall thickness (defined by their outside diameter/inside diameter, or OD/ID). Remaining oligomers or byproducts must be eliminated by careful post-curing, which may require several hours in ventilated ovens at elevated temperatures. Furthermore, silicone tubing in the market is normally translucent and with an inner diameter larger than 300 µm, and thus fails to meet the criteria for micro/cellular scale applications. In contrast, the present invention provides micro-size tubes of inner diameter down to about 4 µm which is smaller than all of the silicon tubing available.

Silicon microchannels and fused silica micro-tubing have been commercialized in the market for years. Although some of the earliest work in microfluidic systems did, in effect, use silicon and glass, these materials have largely been replaced by plastics. For bio-related applications in aqueous solutions, the use of silicon and glass is usually unnecessary and inappropriate. For example, silicon is expensive and opaque to visible and ultraviolet light, and so cannot be used with conventional optical methods of detection. Furthermore, both materials are not permeable to gases and very rigid, thus no corresponding devices such as valving and actuation with peristaltic pumping is possible. In contrast, the present invention provides valving that can be easily realized with mechanical restriction and deformation of the elastomeric microtubes presented herein due to the elastic deformability of these tubes.

Researchers have developed several approaches to fabricate circular microchannels in PDMS as follows: 1) In a combination with standard soft-lithography,[2] a coating of liquid PDMS is applied on the walls of rectangular microchannels, by introducing a pressurized air stream inside the PDMS filled microchannels. Surface tension of the liquid PDMS then forces the coating to take a circular cross-section which is preserved by baking the device under pressure until cured. This method was verified to work on microchannel networks as well as in straight channels and designed diameters can be achieved via proper curing conditions. However, as an extension of the lithography fabrication method, it requires complicated procedures and is hard to fabricate 3D-networked channels. 2) Kim et al. have reported a scheme to fabricate cylindrical microchannels in PDMS based on shaping, bonding and assembly of sucrose fibers.[3] It is simple, cleanroom-free, environmental friendly, and feasible to make complex 3D microchannel architectures. However, the pre-shaped sucrose fiber templates are bonded piece by piece using individual fiber—a tedious and inefficient process. It also raises handling difficulties once the fiber diameter is smaller than 30 µm. Other approaches, such as molding with a liquid cylinder formed on a hydrophilic/hydrophobic patterned surface,[4] can only result in half-cylinder PDMS channels, which raises difficulties in precise alignment of two semi-channels to complete a circular channel. In contrast, the present invention provides a method that is simpler, cheaper and of much higher efficiency to produce microtubes as basic building blocks for microfluidic devices.

Another alternative and competing approach to make 3D microfluidic channels is based on 3D printing technology.[5,7] Generally, 3D micro-cavity networks are formed by either printing 3D sacrificial filament templates that are later leached away after prototypine[7b] or polymerizing the walls of the channel cavities and subsequent drainage of the uncured photopolymer precursor.[7c] Particularly, in one approach exploiting stereolithography, modular and reconfigurable components containing fluidic elements are manufactured to allow rapid assembly of 3D routing of channels.[6] Though elegant, these techniques suffer from the limitation in low printing resolution as the dimension of the "printed" features is limited by the sizes of the nozzle and printing pressure, or by the laser beam diameters, which make it currently a main challenge to produce features smaller than 100 µm.[7a] The rough surface of printed devices also raises a concern for high-resolution imaging in the channels.[7a] Furthermore, the use of rigid materials by 3D printing makes it troublesome to replicate the existing wide variety of PDMS microvalves and micropumps designs. In any case, 3D printing method rely on relatively expensive machines and the cost and time involved in fabricating a single design iteration is still high (about USD 200 per device).[7a] In contrast, in the present invention the total fabrication and material expenses is less than USD 2, representing two orders of magnitudes cut-down in the production cost compared to 3D printing methods.

Micro/nano-tubes can be formed (e.g., rolled up) from thin solid films of inorganic/organic materials at different positions once these films are released from their substrate.[8] These microtubes have been used as 3D cell culture scaffolds[9] and optofluidic sensor.[10] However, both the fabrication and the integration of the microtubes into microfluidic systems require complicated and expensive thermal deposition like Electron Beam deposition and photolithography facilities. In contrast, the present invention provides a simple method of production at a cost savings.

Conventional microfluidic systems made from PDMS are normally fabricated by conventional soft lithography technique. They have been widely used in the study and manipulation of fluids at the submillimeter length scale. Certain properties of microfluidic technologies such as rapid sample processing and the precise control of fluids in an assay have made them attractive candidates to replace traditional experimental approaches in diagnostics and biology research. For example, the invention of 'Quake's valves'[11] among others has led to a plethora of microfluidic designs and publications including the in vitro models "organs-on-chips"[12] and disease-on-a-chip.[13] In contrast, the present invention is not hindered by fabrication methods limited to conventional soft lithography techniques.

Despite the recent increase in research and use of microfluidics, the development of transformative technologies to mitigate the cost of conventional fabrication protocols[14] has not materialized in the past few decades. The high cost is due to the need to use silicon wafer through the photolithography process. The fabrication, testing and redesign period is relatively long. Furthermore, complex multilayered chips require complicated processes involving highly skilled personnel to develop for flow control in lab-on-chip and organ-on-chip systems,[12, 15] thus posing a technology barrier for widely adoption in the biomedical field and industry.

A description of example embodiments of the invention follows. A description of distinctive characteristics that differentiate the present invention from existing technologies also follows.

The PDMS microtubes of the present invention can be specifically used as elementary building blocks for microfluidic devices. The fabrication procedure involves simple mechanical apparatus and cheap common materials readily available in the lab. Except for the same advantages such as biocompatibility, unique mechanical elasticity and chemical inertness as that of silicone tubing, our PDMS microtubes are of micrometer to sub-millimeter sizes and can be easily assembled into more complex devices. It is expected that the microtubes can help to dramatically cut down the cost and time for the design, fabrication and assembly of the microfluidics systems. Moreover, the merit of the versatility of the assembly capability of the elastic microtubes enables one to breakdown complicated microfluidics into organizable functional modules which can significantly lower or even eliminate the technology barrier for more end-users to participate in this microfluidics research as one no longer needs access to an expensive microfabrication lab.

Despite their potential applications in cellular research,[16] PDMS microchannels with circular cross-sectional shapes are currently scarce in the market. The inability to create vascular networks has hindered progress in cardiovascular tissue engineering and organs-on-chip systems for years.[5] Current PDMS micro-channels usually have a rectangular cross-section when fabricated using the conventional fabrication method. The fluid that moves inside such channels does not mimic that of the parabolic-flow profile seen in that of circular cross-section tubes such as that of blood vessels.[17] In the low Reynolds number flow, the velocity and shear stress distribution is expected to be more isotropic in a circular tubular channel than a rectangular one with straight steep walls. The cells flowing inside the latter would experience different mechanical stress depending on their relative positions in the cross-section and due to the anisotropic flow field, leading to disparate cellular activities. The PDMS microtubes of the present invention can have a range of cross-sectional shapes including circular shapes with inner diameter ranging from about 10 μm to about 400 μm. There is space for further scaling down or up. Cells in such a PDMS microtube will experience much more similar stress condition of a natural circulatory system than that of cuboid channels. Moreover, the velocity and vorticity fields in a circular microtube have no corner or singular regions due to the uniform circumferential wall effect.

The microchannels made from the conventional method are fixed in that the microchannels are molded onto PDMS blocks or layers and mounted on rigid glass substrates. The current state-of-the-art technique using the elasticity of PDMS for valving and actuation is represented by the 'Quake's valve'.[11] The Quake's pneumatic valves control the opening and closing of a fluidic channel by an adjacent channel using pneumatic pressure. However, such a complex design requires expertise in high-level soft lithography fabrication, presenting challenges for end-users and the fabrication process is very difficult to automate for mass production.

The PDMS microtube of the present invention provides a unique solution for the valving and actuation in microfluidic devices. The PDMS microtubes are natural self-sustained channels with excellent mechanical elasticity. Flows in PDMS microtubes can be easily turned on or off merely by mechanical deformation. The thickness of the tubular wall is controllable, optically transparent for observation and gas-permeable for oxygen/carbon dioxide. These advantages make it an excellent candidate as scaffolds for realizing "organ-on-chips" and tissue engineering applications.

It is believed that the present invention can meet the urgent need for highly scalable manufacturing of biocompatible microtubes that can be used for microfluidic systems. As the current dominant soft lithography technology in the field of microfluidics not only poses a bottleneck for the industrial adoption due to high cost and time needed, using the present invention as the basic building blocks for PDMS microfluidic systems, one can significantly reduce the cost of fabrication as well as period of manufacture from weeks and days to hours. Thus, the elastomeric microtubes of the present invention can meet the demand for tubular microchannels in the market.

Finally, there is currently no transparent silicone tubing smaller than 300 μm available in the market.

The greatest advantages of the present invention are, for example, ease-of-use, cost effectiveness, various cross-sectional shapes, reconfigurability, and ease in assembling complex 2D and 3D microfluidic systems.

Potential applications of the microtubes of the present invention include the following.

Cell sorting. The margination effect of the metastatic cancer cells in microcirculatory blood flow has been well investigated. The inventors have observed similar margination of white blood cell inside the circular and flexible microtubes. The present inventors have thus proposed to take advantage of the margination effect inside the microtubes to separate diseased cells such as circulating tumor cells (CTCs), bacteria, sickle cell anemia as well as malaria infected red blood cells from blood. This application will open up a great opportunity in the biomedical field such as diseased diagnosis, prognosis, therapy and treatment.

Basic building components for complex 2D and 3D microfluidic systems. Functional microfluidic systems can be made up of microtubes using a pre-designed template with relative ease.

Composite microtubes that can either comprise different materials or are multilayered, e.g., core-shell microtubes which can allow coating of these microtubes depending on the needs of the users.

Additional potential applications of the microtubes of the present invention include, but are not limited to, opto-microfluidics devices, organs-on-chips systems, micropumps/valves for fluidic controls, controlled drug delivery systems, cell stretchers and tissue engineering scaffolds.

Example 1—Method of Making Silicone Elastomer Based Microtube

The method involves immersing a metal wire (normally made of copper or tungsten) vertically into a freshly mixed PDMS (mixture of Sylgard 184 silicone elastomer base and Sylgard 184 silicone elastomer curing agent, 10:1 by weight) or a UV sensitive polymer (MYpolymer, MY-134-XP8, MY Polymers Ltd.) pool, as depicted in FIG. 1A. To fabricate PDMS microtubes, the metal wire was then connected to a variable power supply and heated up to ~100° C. by electricity for 3-5 minutes. This generates a heat field close to the metal wire that initiate PDMS curing. A thin layer of cured PDMS forms on the surface of the wire and its thickness depends on the heating period. The metal wire was then pulled out of the PDMS pool at a speed of ca. 200 µm/s vertically above the fluid level by a linear stepping motor, and a second thin layer of viscous uncured PDMS will form around the wire, which is further cured by hot air at ca. 90-100° C. in a cylindrical heating unit of 10 cm in length and 2 cm in diameter (FIG. 1A). The beading tendency of PDMS[18] during the pulling-out was effectively suppressed by this in situ thermal solidification (FIG. 1A), enabling the production of PDMS microtubes with uniform outer diameters (ODs) (FIG. 1B). The thickness of this second layer is then determined by the pulling speed of the wire and the viscosity and surface tension of the liquid PDMS. The inner diameters (IDs) and cross-sectional shapes of the PDMS microtubes are set by the embedded metal wire diameters and cross-sections (FIGS. 1B and 1C) while the outer diameter can be controlled via changing the pulling speed, the viscosity of the PDMS as well as the heat-up period. The PDMS coated metal wire was cut once it was pulled out to about several tens of centimeters and immersed completely into an acetone solution with sonication for 20 minutes—a process that would extract any unreacted elastomer curing agent and cause slight swelling in the polymer, loosening the PDSM-metal contact. The PDMS microtubes were then detach easily from the metal wires after the acetone treatment. This was followed by baking in a 100° C. oven for one hour to remove any acetone remnant.

Figure 3A:
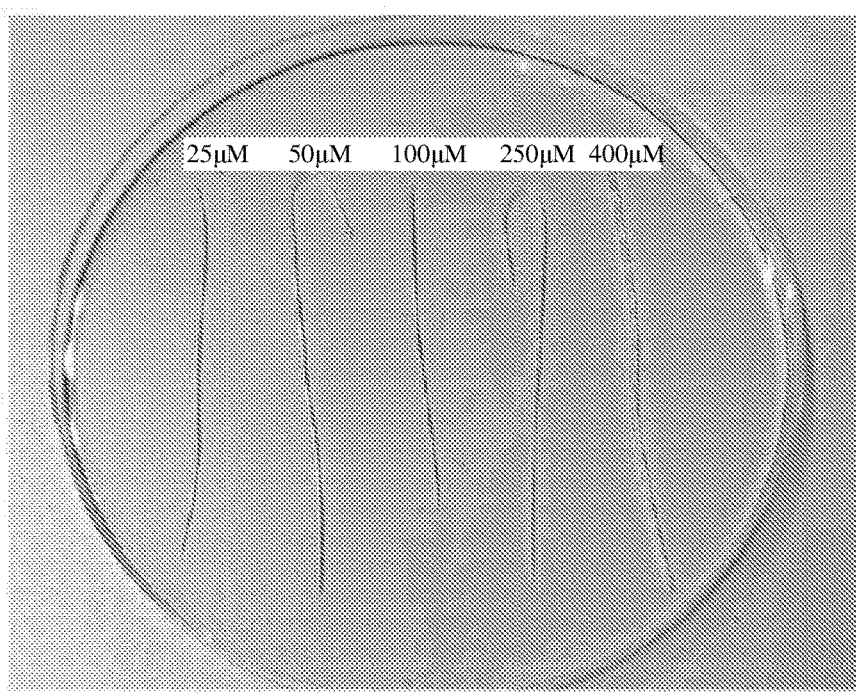
FIG. 3A shows PDMS microtubes with different diameters (25 µm, 50 µm, 100 µm, 250 µm and 400 µm from left to right).
Figure 3B:
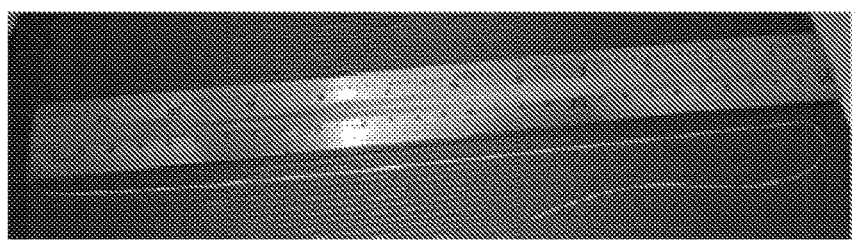
FIG. 3B shows a 50 cm long PDMS microtube with ID=50 µm.

The process is simpler, cleaner and faster than those requiring dissolvable templates.[3, 19] PDMS replicates the contour of the metal wire templates accurately, forming microtubes with the same cross-sections (FIGS. 1C and 2). Thus, the smoothness of inner surface of the microtubes can be evaluated by the contour of the metal wires. FIGS. 2A and 2B are a SEM image and an AFM topography of a Ø=10 µm tungsten wire, respectively, showing the surface of the wire which renders PDMS microtubes of inner roughness of approximately 20-25 nm (FIG. 2C), and of the same ID (FIG. 2D) with good optical transparency (FIGS. 1B and 3A). For circular tubes, typical IDs ranges from 10 to 400 µm (FIG. 1B) and their ODs are controllable by varying certain experimental parameters (see above). Circular microtubes with OD/ID=3:1, 2:1 and 1:1 were repeatedly produced. Despite their high aspect-ratios (up to 4000) and thin walls, the microtubes do not sag or collapse in the middle, showing good self-sustainability. This versatile technique permits the manufacture of self-sustaining microchannels with adequate length (at least half a metre using our laboratory set-ups, FIG. 3B) and various inner diameters and distinct cross-sectional geometries (FIG. 1C).

Notably, this method is readily applied to fabricate microtubes of other polymers.

Example 2—UV Sensitive Polymer Based Microtube

Figure 4:
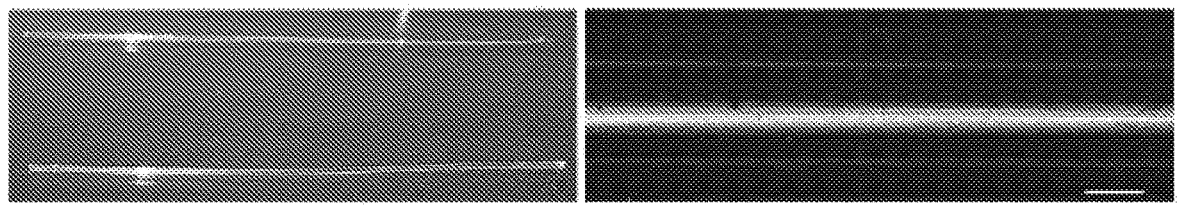
FIG. 4 shows optical images of MYpolymer microtubes with inner diameter of 250 µm (scale bar: 150 µm).

To fabricate MYpolymer microtubes, the metal wire was pulled out of a pre-cured UV-curable MYpolymer pool into an Ar chamber. The thin MYpolymer layer coated around the metal wire was then cured on-site under a UV mercury lamp (350-460 nm, Newport Oriel Product Line System) operating at 300 W with an illumination power of 0.2 W/cm$^2$. The MYpolymer coated metal wire was then transferred into a pure ethanol bath and sonicated for 30 minutes to remove the diffusing photoinitiator. The MYpolymer microtubes (FIG. 4) can then detach from the metal wires after the ethanol treatment, followed by baking in a 100° C. oven for one hour to remove any ethanol remnant.

The mechanical properties of the PDMS microtubes are characterized and listed below when compared with commercially available silicone tubing:

| Property | Unit | Silicone | PDMS microtubes |
| --- | --- | --- | --- |
| Tensile strength | MPa | 6.8-8.7 | 5-10 |
| Elongation at break | % | 570-795 | 200-400 |
| Hardness | Shore | A: 50-80 | A: 43 |
| Brittle temperature | ° C. | −80 | −45 |
| Max. operating temperature | ° C. | +215 | +200 |
| Color | — | Translucent | Clear |

Figure 5A:
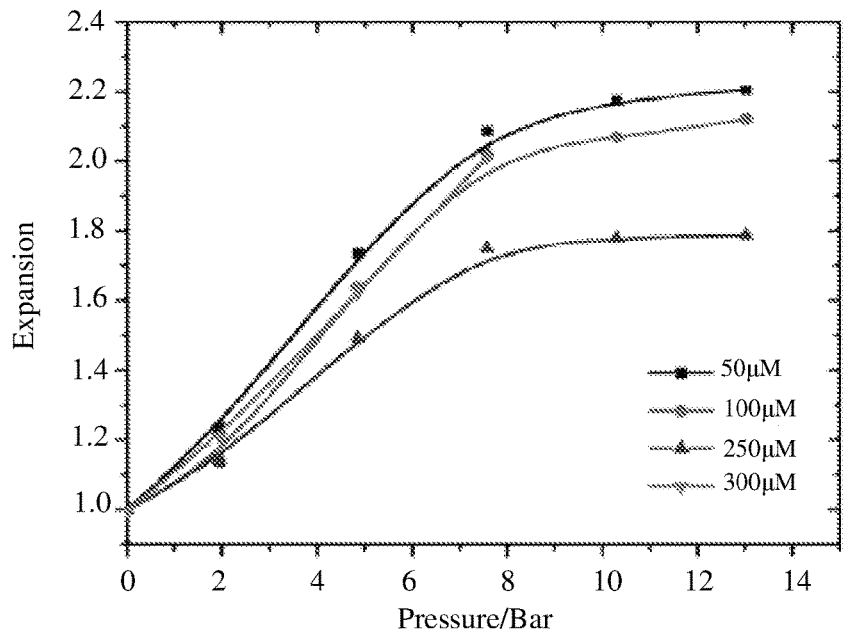
FIG. 5A is a graph showing the normalized expansion of inner diameters of various microtubes as a function of intraluminal pressure (the inner diameters of the microtubes are listed in the lower right corner, the OD/ID ratio is one main factor that influences the tubing expansion, for all the microtubes, OD/ID=2:1).
Figure 5B:
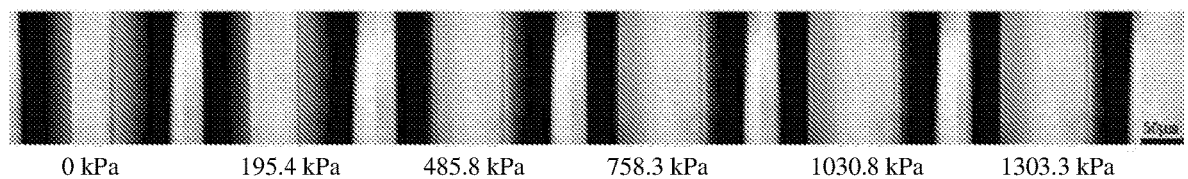
FIG. 5B shows optical images revealing the expansion of the inner diameter of one PDMS microtube (ID=50 µm and OD/ID=2:1) as intraluminal pressure increases. Scale 50 µm.

Though much smaller in the diameters, the PDMS microtubes show similar properties as commercial available silicon tubings with slightly better tensile strength. The properties of self-sustaining allow the hollow microtubes to convey substances that can flow—liquids and gases. Notably, when the intraluminal pressure is increased to more than 10 bar, the PDMS microtubes (OD/ID=2:1) expanse about two folds in the IDs (FIG. 5) without bursting and can return to their original shape reversibly after being deformed—indicating excellent elasticity.

For demonstration of application, the PDMS microtubes were used as an example. In principle, MYpolymer microtubes will have similar application as that of PDMS microtubes.

Example 3—PDMS Microtubes as Basic Microfluidic Components (Pipe, Valve and Pump)

The PDMS cured under our experimental condition normally has a Young's modulus of 1.5-2.0 MPa, allowing significant deflections with moderate actuation forces. This property then provides a unique solution for the valving and actuation for microtube-based microfluidic devices. Flows in these microtubes can be easily controlled merely via mechanical compression and release on them by a commercially available mechanical pincher on the pipeline (FIGS. 6A and 6B). Microtubes with circular cross-section were used for the implementation of valving due to the fact that the rounded channels close from edges to center by external compressional force and thus seal completely at lower pressure in comparison to rectangular and square channels.[11] The control of flows with an on-off valve is demonstrated in FIG. 6A. The mechanical pinch point that crosses over the microtubes is normally 0.5 mm in the width and for a microtube with an ID=100 µm, the switching valve has a dead volume of about $\pi \times 50$ µm$\times 50$ µm$\times 500$ µm=3950 pl—comparable to PDMS valves fabricated by soft-lithography method[11] and about four orders of magnitude smaller than 3D printed valves.[20] The valve responds instantaneously to the on and off of the mechanical switch without any lag behind the control signal that is endemic to pneumatic valves.[11, 20] This advantage enables it to be operated at nearly 75 Hz—the limit of the hardware and no signs of rupture or fatigue after more than 20000 cycles of actuations were observed. The typical pressure that drives the valve to close is on the order of 100 kPa and higher back pressure can be countered by simply increasing the applied pincher pressure.

Figure 7A:
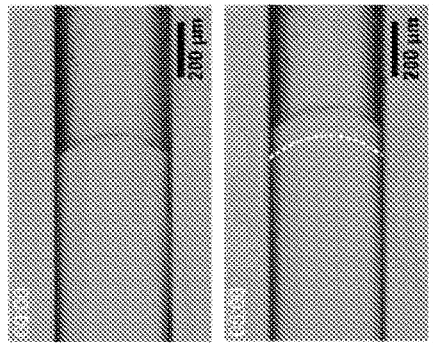
FIG. 7A is a schematic representation of a peristaltic pump compressing a PDMS microtube (indicated by the white-only arrow) with ID of 100 µm, wherein the rotor (indicated by the black arrow) occludes the flexible microtube and forces the fluid to be pumped to move through (black-outlined-white arrows) the tube as it turns (circular arrow), and wherein the differences in pumping rate were achieved by rotating the rotor at various speeds.
Figure 7B:
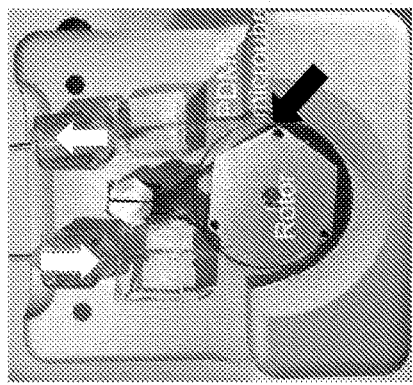
FIG. 7B is a photo of the device schematically presented in FIG. 7A, wherein a PDMS microtube with ID=100 µm (indicated by the black arrow) was bound around the motor and the white arrows indicate the flow direction inside the tube.
Figure 7C:
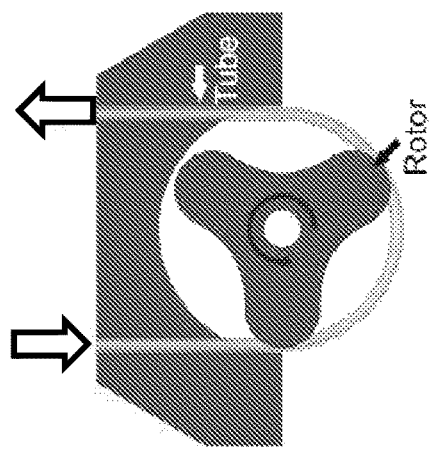
FIG. 7C shows time lapse images of the advancing fluid front in a time period of 5 minutes in the outlet of the peristaltic pump shown in FIG. 7B.
Figure 7D:
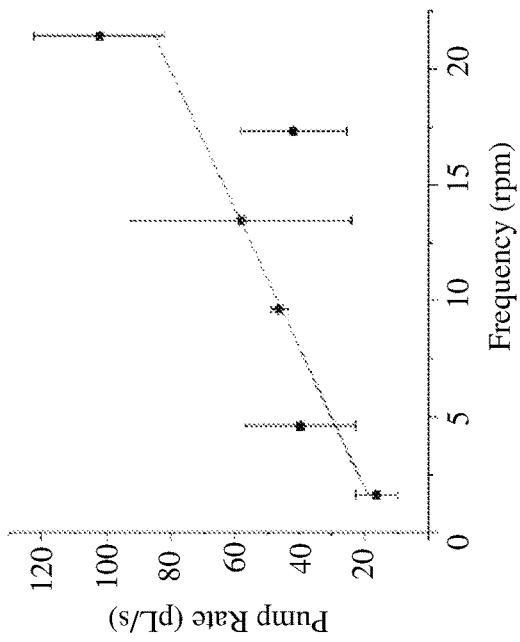
FIG. 7D is a graph showing the pumping rate of the peristaltic pump versus rotating speed (with an ID=100 µm microtube) wherein a flow rate of ~100 pL/s or below can be easily achieved which is one to two orders of magnitude lower than the same peristaltic pump using commercially available small size tubes (380 µm ID tube, INSTECH pump user manual).

Similarly, a peristaltic pump was realized by replacing the pumping tube with a single circular PDMS microtube with ID=100 μm (FIGS. 7A and 7B). The motion of a column of water in the outlet tubing (0.5 mm ID) was used to calculate the pumping rate and a maximum pumping rate of 100 pl/s was achieved, which is comparable to microfluidic pumps published in the literature previously.[11] The greatest advantage of the system of the present invention is its ease of production. In contrast to the complicated and multiple layered microvalve and micropump systems fabricated by soft-lithography[11, 21] and stereolithography,[20, 22] the valve and pump of the present invention have much simpler structure and can be easily assembled with commercial available mechanical switches. Furthermore, they require no significant engineering expertise and extra hydromantic pressure system to function.

Figure 8A:
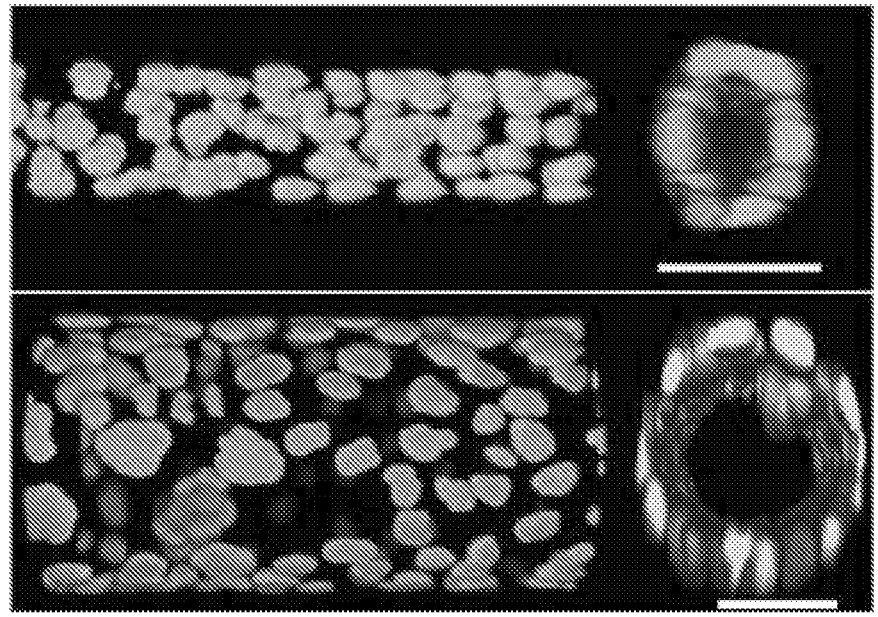
FIG. 8A shows fluorescent images of nuclei of epithelial cells grown in PDMS microtubes (IDs: top, 50 µm and bottom, 100 µm) for 24 hours (left: side view; right: cross-sectional view, scale bars: 50 µm).

Example 4—PDMS Microtubes as 3D Cell Culture Scaffolds and to Mimic In Vivo Flow Profile of Blood The PDMS microtubes are biocompatible and permeable to gases and thus can be used as in vitro 3D culture scaffolds. The inner surface of circular microtubes (ID=50 and 100 μm) were coated with fibronectin and grow adherent epithelial cells inside. FIG. 8A shows fluorescent images of the cells attached to the inner surface of the microtubes, forming a tubular cell sheet. The merits of transparency, biocompatibility and flexibility of the microtubes further allow the investigation of detailed cellular processes under stress and in vivo similar microenvironments—a step forwards tissue engineered microfluidic organ-on-a-chip.

Figure 8B:
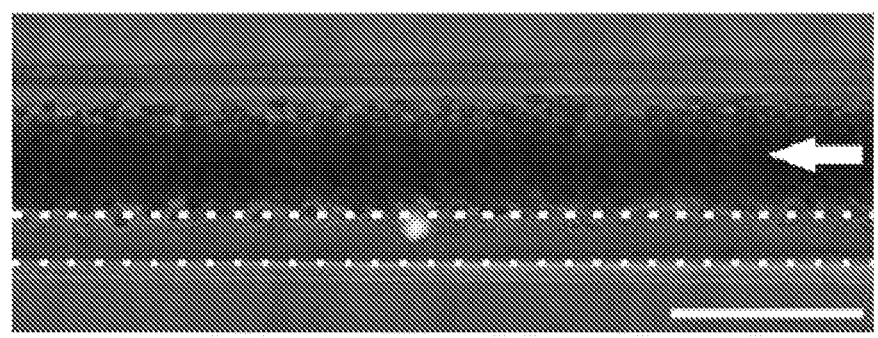
FIG. 8B is a typical optical image showing margination effect in a circular microtube with ID=25 µm wherein epithelial cells were mixed with red blood cells at 40% hematocrit and the white arrow indicates the flow direction and the concentrated red blood cells in the middle of the tube, and wherein a white blood cell flowing in the RBC-free zone (between the two white dash lines) near the tube walls is shown (scale bar: 25 µm).

The advantage of using microfluidics as a platform for tissue engineering and drug screening is its ability to finely regulate fluid flow conditions, including flow rate, shear stress and pulsatile flow, while also providing means for modifying the networks of vessels, the type of surface of inner walls, and for patterning cells in 3D tissue-like architecture, including generation of lumen walls lined with cells. With the microtubes of different cross-sectional shapes, the present invention is able to mimic cardiovascular flow conditions. By flowing whole blood into flexible circular microtubes of the present invention, the flow profile of cells through small size blood capillaries is able to be mimicked (FIG. 8B). The margination of bigger cells (herein, white blood cells) toward walls in the flow (FIG. 8B) was clearly observed—a phenomenon similar to in vivo conditions.[23] Particle margination is mediated by red blood cells (RCBs), which tend to migrate to the vessel centre due to hydrodynamic interactions with the walls (lift force), resulting in a RCB-free layer near the walls.[24] In brief, margination is a consequence of the competition between lift forces on RCBs and suspended particles and their interactions in flow[25] and understanding its characteristics has important implication in efficient drug delivery. With the flexible and circular microtube, it now allows one to accurately mimic the flow of cells through the blood capillaries and to study the behavior of individual cells and cell suspensions under dynamic conditions.

Figure 9A:
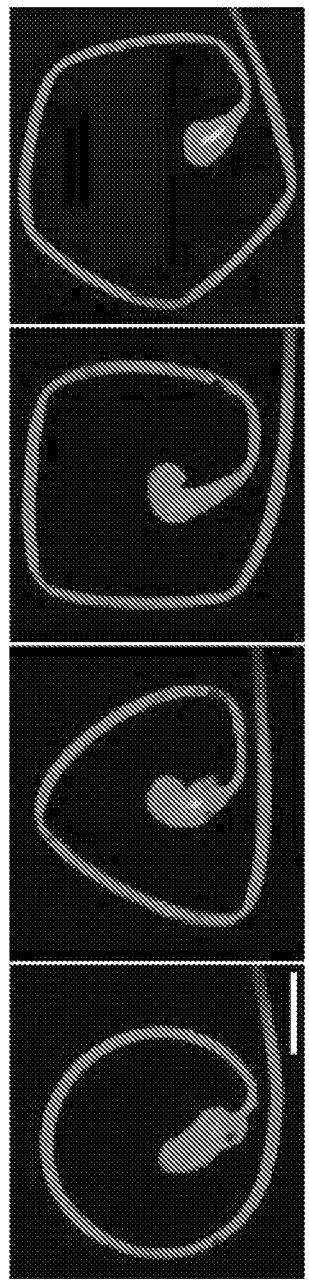
FIG. 9A shows fluorescent images of 2D microchannels having circular, rectangular, square and pentagon shapes (from left to right), respectively, wherein the PDMS microtubes used have ID of 50 µm (scale bar: 400 µm). Microchannels of varying 2D geometries can be easily created by bending the PDMS microtubes, wherein the microtubes were filled with aqueous solutions of fluorescein, winded up using pre-manufactured (either by mechanical cutting or 3D printing) frameworks and imaged with a confocal microscope.
Figure 9B:
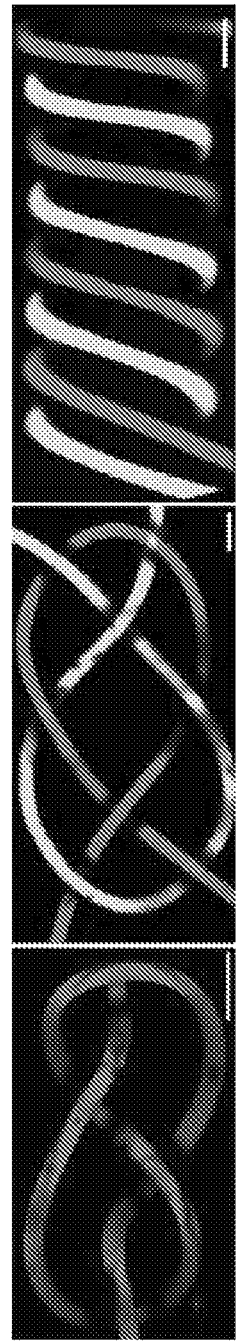
FIG. 9B shows optical micrographs of pseudo-3D microstructures having the shape of a figure-8 knot (left), a Carrick bend (middle) and a double spiral (right) (scale bars: 150 µm). Microchannels of varying pseudo-3D geometries can be easily created by bending the PDMS microtubes, wherein the microtubes were filled with aqueous solutions of fluorescein, winded up using pre-manufactured (either by mechanical cutting or 3D printing) frameworks and imaged with a confocal microscope.

Example 5—Fast Assembly of 2D and 3D Functional Microfluidic Channels Using Flexible PDMS Microtubes The good elasticity of the present invention allows one to bend the PDMS microtubes into almost any 2D and 3D geometries (FIG. 9). FIG. 9A presents the 2D microchannels (circular cross-section, ID=50 μm) with circular, triangular, square and pentagon shapes. In addition, the approach of the present invention enables the fast patterning of 3D microchannels with pre-manufactured (through mechanical cutting or 3D printing) frameworks. FIG. 9B demonstrates the formation of pseudo-3D channels with the microtubes by simply bending and fixing a microtube into a 3D shape. FIG. 9B left shows channels made from an ID=50 μm tube tied in the shape of a figure-eight knot. The size of the smallest knot was determined by the actual size of the microtubes (the OD) and the knot in FIG. 9B occupied a volume of 0.5× 0.85×0.3 mm$^3$. Other pseudo-3D channels such as Carrick bend and double spiral (FIG. 9B) can be produced by similar method with or without a template. The use of a template can assist in positioning microtubes in specific 3D orientations and a collapse or sag in the middle of the tubes due to the bending was not observed.

Figure 10A:
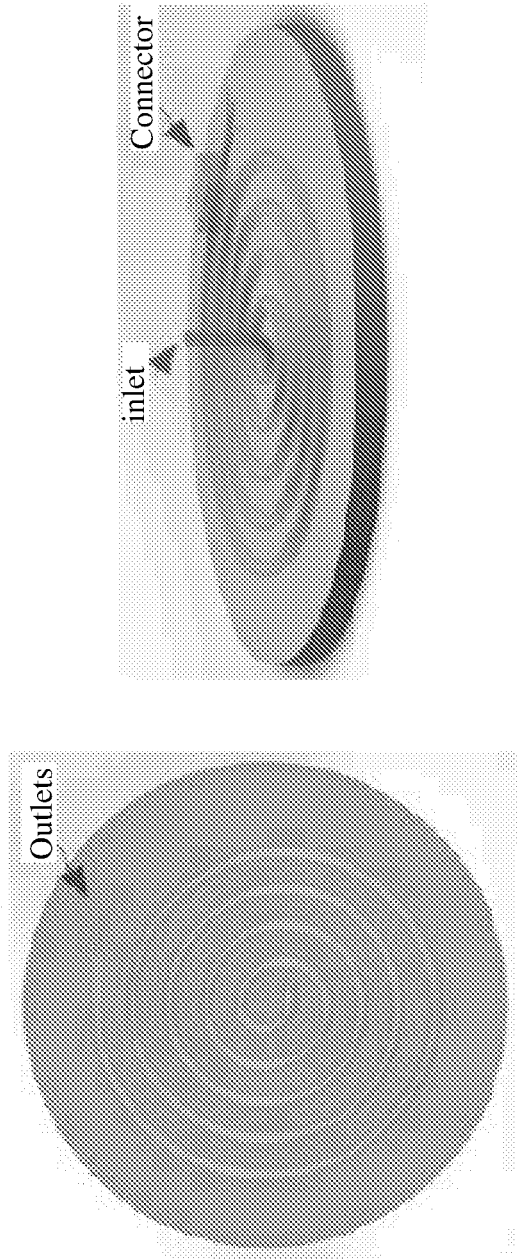
FIG. 10A shows schematic views of a spiral microchannel made from the PDMS microtube (left is top view and right is side view).
Figure 10B:
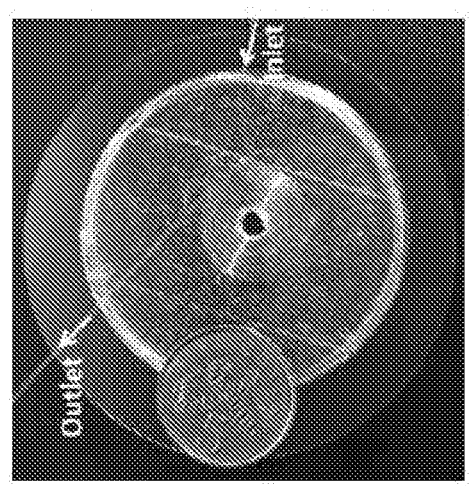
FIG. 10B is an optical image showing spiral microfluidic channels made from a PDMS microtube with inner diameter of 100 µm.
Figure 11A:
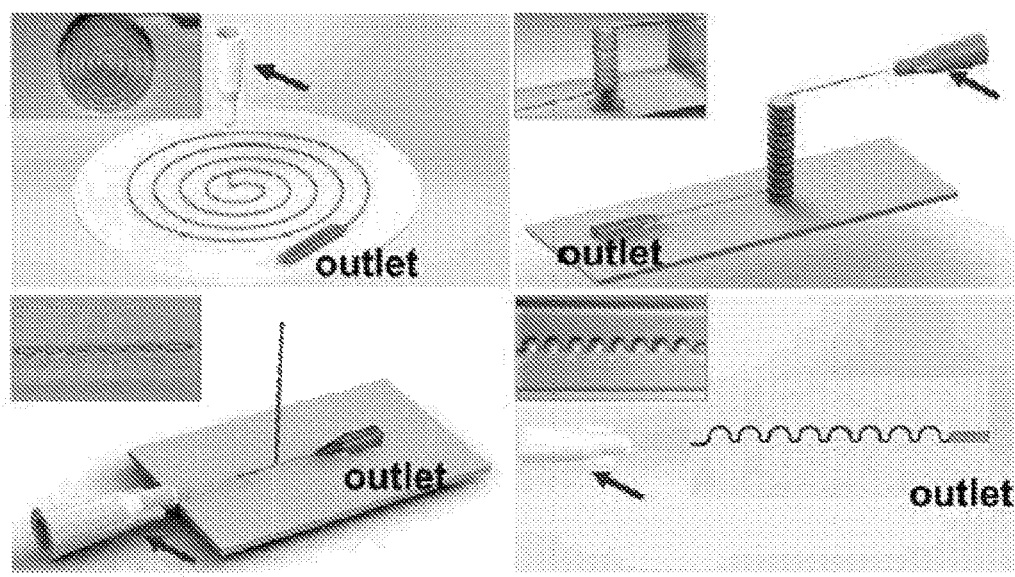
FIG. 11A shows four different configurations of microtubes forming microfluidic chips that realize particle focusing wherein the microtubes with 100 µm ID were configured into 2D spiral in a plane, 3D spiral around a cylinder, 3D twisting and 2D serpentine shape (black arrows indicate inlets and black text shows the outlets). The inserts are photos of the channels.

As a proof-of-concept on the applications of the microtubes, a spiral microchannel device with potential applications for microparticles or cells sorting was produced (FIGS. 10 and 11). Spiral channel microfluidics were first introduced by Professor Lim Chwee Teck's group, one of the inventors, to successfully separate a handful of circulating tumor cells (CTCs) from billions of blood cells.[26] They further improved the spiral chips by changing the cross-section of the channel from cuboid to slanted for better sorting efficiency.[27] Nevertheless, according to Kalpakli et al.,[28] a curved channel with circular cross-section has the highest through-put with apparent different vorticity regions which is much more efficient in sorting than rectangular or slanted shape microchannels.

Figure 11B:
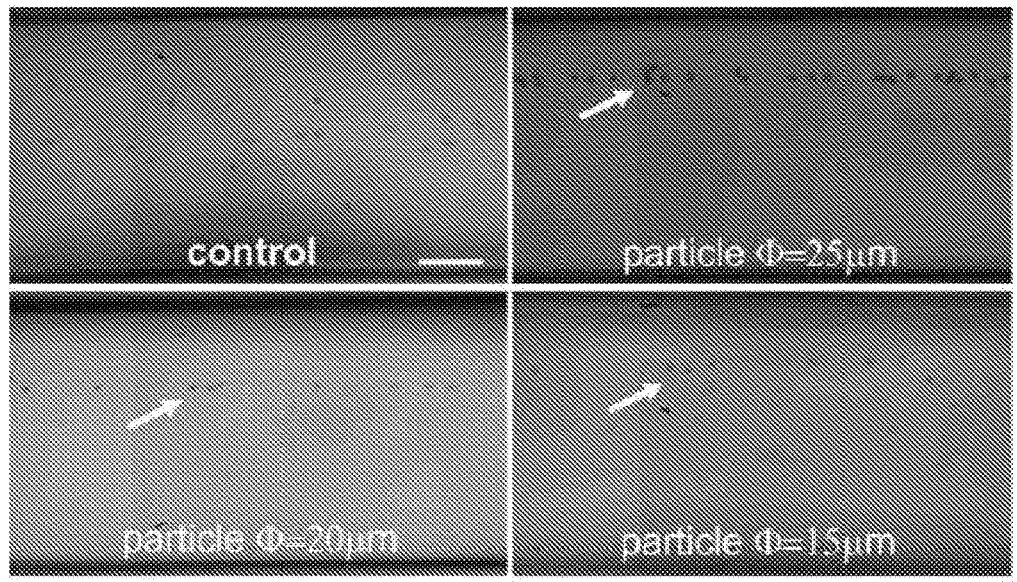
FIG. 11B shows microparticles of different diameters (white text at the bottom of each image) were focused (indicated by the white arrows) after flowing through the devices shown in FIG. 11A, wherein the control shows particles flowing through a straight tube without any special patterns (the flow speeds were 800, 500 and 400 µl/min for particles of 25, 20 and 15 µm in diameters, respectively, scale bar: 150 µm).
Figure 11C:
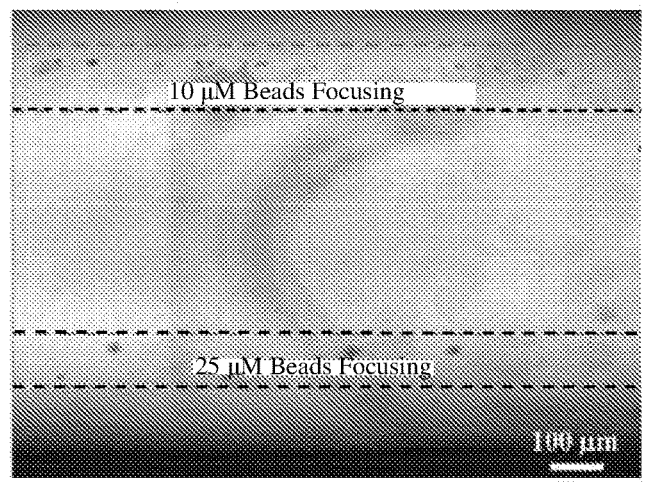
FIG. 11C is an optical image that shows that particles of 10 and 25 µm in diameter flow in separate tracks in the outlet of a 3D spiral chip (the flow speed was 200 µl/min).

By carefully balancing the shear/wall-induced lift forces and the lateral Dean drag force in circular curvilinear channels,[29] several microfluidic chips using PDMS microtubes of ID=100 μm (FIG. 11A) were designed and fabricated, which show the capability of microparticles (ranging from 15 to 25 um in diameter) focusing in flow rates of 200-1200 μl/min (FIG. 11B). The designs (IDs and the radius of curvature of the channels) of the asymmetric channels satisfies the preconditions of $a/D_h>0.07$ and $D_e>20$, where a being the particle diameter, $D_h$, the hydraulic diameter, and $D_e$, the Dean number.[29] In a cylindrical tube, particles were observed to migrate away from the tube center and walls to form a focus annulus, however in asymmetric curvilinear channels a lateral Dean drag flow results in the reduction of the annulus to single particle streams[29] (FIG. 11B). Although the assembly of the spiral chips is currently manual, it normally takes less than 20 min to produce one chip. It is emphasized here that these chips that cover an area of ca. 2 cm$^2$ were fabricated completely outside a cleanroom with much less cost in time and resources. Furthermore, it was possible to focus particles of various diameters to particular streamline in the same flow (FIG. 11C), and thus it allows different pure fractions to be collected through the use of multiple outlets. For an operational flow rate of 200 μl/min of 1% particle solution a mass sorting rate of ≈0.125 g/hr is achieved for one hand-made spiral chip, while for typical of most microfluidic systems, a throughput of 30 mg/hr was described for deterministic displacement.[30] The increase of one order of magnitude in throughput by the devices of the invention shows promising applications in diagnostic separation and filtration of our PDMS microtubes.

Figure 12A:
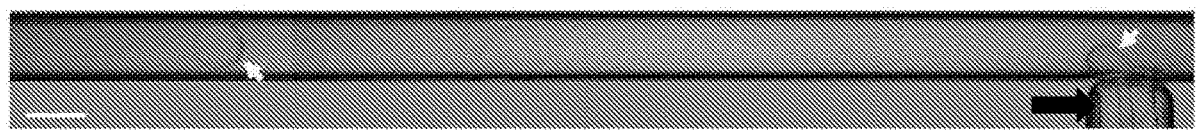
FIG. 12A illustrates droplet generation using microtubes. A microtube (ID of 50 µm) was inserted into a pre-made T-junction wherein oil was flowing through the horizontal channel whereas water was flowing out of the microtube (indicated by the black arrow) such that this configuration enables generating monodisperse microdroplets (here, water droplets indicated by the white arrows) in a high-throughput mode (scale bar: 200 µm).
Figure 12B:
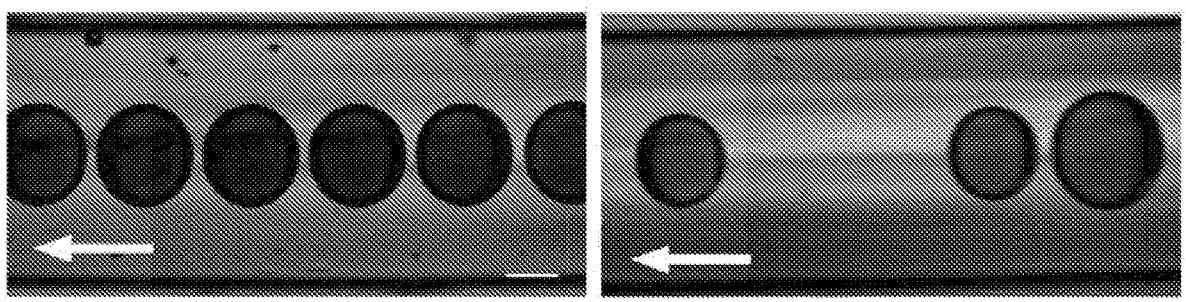
FIG. 12B illustrates droplet generation using microtubes. Optical images showing the water droplets of a uniform diameter in a continuous oil flow (left image) and water droplets of changing diameters in an interrupted oil flow (right image) wherein the white arrows indicate the flow direction (scale bar: 100 µm).

Furthermore, the ability to rapidly assemble and modify a common microfluidic circuit topology—T junction[31] used to generate droplets has been demonstrated. An important subcategory of microfluidics is droplet-based microfluidics.[32] Unlike continuous flow systems, droplet-based devices focus on creating discrete volumes in an immiscible phase. Applications where droplet based microfluidics are used include chemical reaction, therapeutic agent delivery, chemical analysis and diagnostic testing.[31] T-junction can be implemented simply by connecting two PDMS tubes to a commercial available plastic T-shape connector, but for imaging convenience, two ID=100 μm microtubes were inserted into a millimeter size PDMS T-junction that was made by single-step molding with metal rods as templates (FIG. 12A). Two syringe pumps were used to drive carrier oil and water streams into the circuit. The circuit operated well at aqueous flow rate above 1 μl/min and carrier flow rate higher than 500 μl/min, and generated water microdroplets ranging from 200 to 500 μm in diameter in a range of frequency (30 to 500 Hz, FIG. 12A). In addition, by controlling the oil flow, discrete water droplets of a uniform diameter or of diverse diameters (FIG. 12B) can be produced with this simple set-up.

It is believed that the elastomeric microtube of the present invention is going to make a significant impact and radically changes how microfluidic systems can be designed, fabricated and used. Also, currently there is no transparent silicone tubing smaller than 300 μm available in the market. It is expected that there will be immediate demand for these microtubes from researchers and developers of microfluidic devices. In fact, these microtubes will provide new avenues in the study of microfluid dynamics and new applications in lab-on-chips and organs-on-chips as well as flexible microfluidics.

REFERENCES

1. Colas, A., *Chimie Nouvelle* 1990, 8 (30), 847.
2. Abdelgawad, M., et al., A fast and simple method to fabricate circular microchannels in polydimethylsiloxane (PDMS). *Lab Chip* 2011, 11 (3), 545-551.
3. Lee, J., et al., Sucrose-based fabrication of 3D-networked, cylindrical microfluidic channels for rapid prototyping of lab-on-a-chip and vaso-mimetic devices. *Lab Chip* 2012, 12 (15), 2638-2642.
4. De Ville, M., et al., Simple and low-cost fabrication of PDMS microfluidic round channels by surface-wetting parameters optimization. *Microfluid. Nanofluid.* 2012, 12 (6), 953-961.
5. Kolesky, D. B., et al., 3D Bioprinting of Vascularized, Heterogeneous Cell-Laden Tissue Constructs. *Adv. Mater.* 2014, 26 (19), 3124-3130.
6. Bhargava, et al., N., Discrete elements for 3D microfluidics. *Proc. Natl. Acad. Sci. USA* 2014, 111 (42), 15013-15018.
7. (a) Au, A. K.; Lee, W.; Folch, A., Mail-order microfluidics: evaluation of stereolithography for the production of microfluidic devices. *Lab Chip* 2014, 14 (7), 1294-1301; (b) Miller, J. S., et al., Rapid casting of patterned vascular networks for perfusable engineered three-dimensional tissues. *Nat. Mater.* 2012, 11 (9), 768-774; (c) Kitson, P. J., et al., Configurable 3D-Printed millifluidic and microfluidic 'lab on a chip' reactionware devices. *Lab Chip* 2012, 12 (18), 3267-3271; (d) Derby, B., Printing and Prototyping of Tissues and Scaffolds. *Science* 2012, 338 (6109), 921-926.
8. Schmidt, O. G.; Eberl, K., Nanotechnology: Thin solid films roll up into nanotubes. *Nature* 2001, 410 (6825), 168-168.
9. Xi, W., et al., O. G., Rolled-up Functionalized Nanomembranes as Three-Dimensional Cavities for Single Cell Studies. *Nano Lett.* 2014, 14 (8), 4197-4204.
10. Harazim, S. M., et al., Lab-in-a-tube: on-chip integration of glass optofluidic ring resonators for label-free sensing applications. *Lab Chip* 2012, 12 (15), 2649-2655.
11. Unger, M. A., et al., Monolithic Microfabricated Valves and Pumps by Multilayer Soft Lithography. *Science* 2000, 288 (5463), 113-116.
12. Bhatia, S. N.; Ingber, D. E., Microfluidic organs-on-chips. *Nat. Biotech.* 2014, 32 (8), 760-772.
13. Zervantonakis, I. K., et al., Three-dimensional microfluidic model for tumor cell intravasation and endothelial barrier function. *Proc. Natl. Acad. Sci. USA* 2012, 109 (34), 13515-13520.
14. Englert, D. L., et al., Investigation of bacterial chemotaxis in flow-based microfluidic devices. *Nat. Protocols* 2010, 5 (5), 864-872.
15. Weaver, J. A., et al., Static control logic for microfluidic devices using pressure-gain valves. *Nat Phys* 2010, 6 (3), 218-223.
16. Wong, A. D.; Searson, P. C., Live-Cell Imaging of Invasion and Intravasation in an Artificial Microvessel Platform. *Cancer Res.* 2014, 74 (17), 4937-4945.
17. Whitesides, G. M., The origins and the future of microfluidics. *Nature* 2006, 442 (7101), 368-373.
18. Grilli, S., et al., 3D lithography by rapid curing of the liquid instabilities at nanoscale. *Proc. Natl. Acad. Sci. USA* 2011, 108 (37), 15106-15111.
19. Lee, J.; Kim, J., Elastomeric microwire-based optical gas flowmeter with stretching-enabled tunability in measurement range. *Opt. Lett.* 2011, 36 (19), 3789-3791.
20. Au, A. K., et al., 3D-printed microfluidic automation. *Lab Chip* 2015, 15 (8), 1934-1941.
21. Weaver, J. A., et al., Static control logic for microfluidic devices using pressure-gain valves. *Nat. Phys.* 2010, 6 (3), 218-223.
22. Rogers, C. I., et al., 3D printed microfluidic devices with integrated valves. *Biomicrofluidics* 2015, 9 (1), 016501.
23. Goldsmith, H. L.; Spain, S., Margination of leukocytes in blood flow through small tubes. *Microvasc. Res.* 1984, 27 (2), 204-222.
24. Cantat, I.; Misbah, C., Lift Force and Dynamical Unbinding of Adhering Vesicles under Shear Flow. *Phys. Rev. Lett.* 1999, 83 (4), 880-883.
25. Kumar, A.; Graham, M. D., Mechanism of Margination in Confined Flows of Blood and Other Multicomponent Suspensions. *Phys. Rev. Lett.* 2012, 109 (10), 108102.
26. Hou, H. W., et al., Isolation and retrieval of circulating tumor cells using centrifugal forces. *Sci. Rep.* 2013, 3.
27. Warkiani, M. E., et al., Slanted spiral microfluidics for the ultra-fast, label-free isolation of circulating tumor cells. *Lab Chip* 2014, 14 (1), 128-137.
28. (a) Kalpakli, A., et al., Dean vortices in turbulent flows: rocking or rolling? *J Vis* 2012, 15 (1), 37-38; (b) Kalpakli, A. Experimental study of turbulent flows through pipe bends. PhD Thesis, KTH Mechanics, Stockholm, Sweden, 2012.
29. (a) Hou, H. W., et al., Isolation and retrieval of circulating tumor cells using centrifugal forces. *Scientific Reports* 2013, 3, 1259; (b) Di Carlo, D., et al., Continuous inertial focusing, ordering, and separation of particles in microchannels. *Proc. Natl. Acad. Sci. USA* 2007, 104 (48), 18892-18897.
30. Davis, J. A., et al., Deterministic hydrodynamics: Taking blood apart. *Proc. Natl. Acad. Sci. USA* 2006, 103 (40), 14779-14784.
31. Teh, S.-Y., et al., *Droplet microfluidics. Lab Chip* 2008, 8 (2), 198-220.
32. Atencia, J.; Beebe, D. J., Controlled microfluidic interfaces. *Nature* 2005, 437 (7059), 648-655.

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. A method of making a flexible microtube comprising a polymer, the method comprising:
    immersing a wire into a pool comprising heat curable polymer;
    heating the wire for a first period of time, thereby initiating curing of the heat curable polymer at the surface of the wire;
    pulling the wire out of the pool;
    heating the wire for a second period of time, thereby curing additional heat curable polymer and producing a polymer coated wire;
    immersing the polymer coated wire in a liquid bath with sonication, thereby loosening the polymer-wire contact;
    removing the wire from the polymer coated wire, thereby producing a polymeric microtube; and
    heating the polymeric microtube, thereby producing the flexible microtube.

2. The method of claim 1, wherein the flexible microtube comprising a polymer has an inner diameter of about 4 μm to about 1000 μm, and a variable outer diameter.

3. The method of claim 1, wherein the polymer is a silicone elastomer, an ultraviolet sensitive polymer, a conductive polymer, polyurethane, a thermoplastic polymer, a thermoset polymer, a polyimide, or a conductive rubber.

4. The method of claim 3, wherein the silicone elastomer is polydimethylsiloxane, phenyl-vinyl silicone, methyl-siloxane, platinum cured silicone rubber or fluoro-siloxane.

5. The method of claim 3, wherein the ultraviolet sensitive polymer is a fluorinated resin with acrylate/methacrylate groups, styrene-acrylate-containing polymer, polyacrylate polyalkoxy silane, a positive photoresist or a negative photoresist.

6. The method of claim 1, wherein the microtube inner diameter is between about 10 μm and about 800 μm.

7. The method of claim 1, wherein the length of the microtube is about 10 m or less.

8. The method of claim 1, wherein the microtube is gas permeable.

9. The method of claim 1, wherein the microtube is transparent.

10. The method of claim 1, wherein the microtube is biocompatible.

11. The method of claim 1, wherein
    the heating for a first period of time is performed via electric current along the wire,
    the heating for a second period of time is performed via a hot air heating element,
    the liquid bath is an acetone bath, and
    the heating of the polymeric microtube is performed via baking.

12. The method of claim 1, wherein the microtube has a circular, rectangular, square, triangular, elliptical, star or irregular cross-sectional shape.

\* \* \* \* \*